(12) United States Patent
Kawanami et al.

(10) Patent No.: US 8,901,345 B2
(45) Date of Patent: Dec. 2, 2014

(54) PROCESS FOR PREPARATION OF OPTICALLY ACTIVE DIAMINE DERIVATIVE SALT

(71) Applicant: Daiichi Sankyo Company, Limited, Tokyo (JP)

(72) Inventors: Koutarou Kawanami, Kanagawa (JP); Hideaki Ishikawa, Kanagawa (JP); Masahiro Shoji, Kanagawa (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/732,857

(22) Filed: Jan. 2, 2013

(65) Prior Publication Data

US 2013/0165657 A1 Jun. 27, 2013

Related U.S. Application Data

(63) Continuation of application No. PCT/JP2011/065192, filed on Jul. 1, 2011.

(30) Foreign Application Priority Data

Jul. 2, 2010 (JP) ................................. 2010-151922

(51) Int. Cl.
| | | |
|---|---|---|
| C07C 261/00 | (2006.01) | |
| C07C 269/00 | (2006.01) | |
| C07C 271/00 | (2006.01) | |
| C07C 55/07 | (2006.01) | |
| C07C 51/43 | (2006.01) | |
| C07D 417/04 | (2006.01) | |
| C07C 269/08 | (2006.01) | |
| C07D 513/04 | (2006.01) | |
| A61K 31/44 | (2006.01) | |
| C07D 513/02 | (2006.01) | |
| C07D 515/02 | (2006.01) | |
| C07D 471/02 | (2006.01) | |
| C07D 491/02 | (2006.01) | |
| C07D 498/02 | (2006.01) | |

(52) U.S. Cl.
CPC .............. *C07C 269/08* (2013.01); *C07C 55/07* (2013.01); *C07C 51/43* (2013.01); *C07D 417/04* (2013.01); *C07D 513/04* (2013.01)
USPC ........................... 560/115; 546/144; 514/301

(58) Field of Classification Search
CPC .. C07D 495/04; C07D 513/04; C07D 333/20; C07C 271/22; C07C 2101/14; C07C 271/06
See application file for complete search history.

(56) References Cited

U.S. PATENT DOCUMENTS

| | | | | |
|---|---|---|---|---|
| 4,582,570 A | * | 4/1986 | Mix | ................................. 203/16 |
| 5,055,600 A | | 10/1991 | Wagner | |
| 5,149,855 A | | 9/1992 | Sakimae et al. | |

(Continued)

FOREIGN PATENT DOCUMENTS

| | | |
|---|---|---|
| JP | 4-227629 | 8/1992 |
| JP | 11-180899 | 7/1999 |

(Continued)

OTHER PUBLICATIONS

Dean, Ja. Lange's Handbook of Chemistry. McGraw-Hill, Inc. 1999, 15th Ed., p. 5.62, Table 5.11.*

(Continued)

*Primary Examiner* — Rita Desai
*Assistant Examiner* — Ben S Michelson
(74) *Attorney, Agent, or Firm* — Locke Lord, LLP

(57) ABSTRACT

The problem to be solved is to produce, at high yields with high purity, anhydrous crystals of a compound represented by formula (1) that is an important intermediate for preparation of FXa inhibitor compound (X) or a pharmacologically acceptable salt thereof, or a hydrate thereof. The solution thereto is an industrial preparation process that provides, with high purity, anhydrous crystals of a compound represented by the following formula (1), which is an intermediate for the production of FXa inhibitor compound (X) or a pharmacologically acceptable salt thereof, or a hydrate thereof, wherein Boc represents a tert-butoxycarbonyl group.

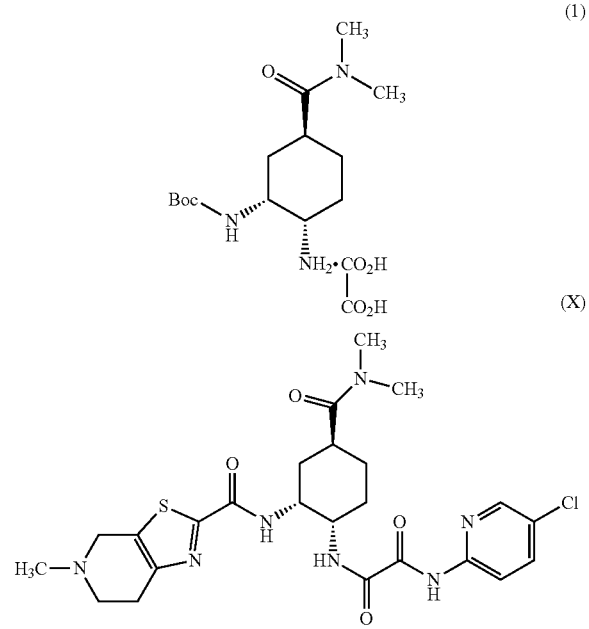

12 Claims, 9 Drawing Sheets

(56) References Cited

U.S. PATENT DOCUMENTS

| | | | |
|---|---|---|---|
| 5,677,469 | A | 10/1997 | van Eikeren et al. |
| 7,192,968 | B2 | 3/2007 | Yoshino et al. |
| 7,342,014 | B2 | 3/2008 | Ohta et al. |
| 7,365,205 | B2 | 4/2008 | Ohta et al. |
| 7,576,135 | B2 | 8/2009 | Ohta et al. |
| 7,674,904 | B2 | 3/2010 | Doshan et al. |
| 2004/0122063 | A1 | 6/2004 | Yoshino et al. |
| 2005/0020645 | A1 | 1/2005 | Ohta et al. |
| 2005/0119486 | A1 | 6/2005 | Ohta et al. |
| 2005/0245565 | A1 | 11/2005 | Ohta et al. |
| 2006/0252837 | A1 | 11/2006 | Ohta et al. |
| 2006/0275357 | A1 | 12/2006 | Oomura et al. |
| 2007/0135476 | A1 | 6/2007 | Nagasawa et al. |
| 2008/0015215 | A1 | 1/2008 | Ohta et al. |
| 2009/0105491 | A1 | 4/2009 | Sato et al. |
| 2009/0192313 | A1 | 7/2009 | Nagasawa et al. |
| 2009/0270446 | A1 | 10/2009 | Ohta et al. |
| 2009/0281074 | A1 | 11/2009 | Ohta et al. |
| 2010/0081685 | A1 | 4/2010 | Kojima et al. |

FOREIGN PATENT DOCUMENTS

| | | |
|---|---|---|
| JP | 2000-344735 | 12/2000 |
| JP | 2001-151724 | 6/2001 |
| JP | 2008-542287 | 11/2008 |
| JP | 2010-254615 | 11/2010 |
| WO | 01/74774 | 10/2001 |
| WO | 03/000657 | 1/2003 |
| WO | 03/000680 | 1/2003 |
| WO | 03/016302 | 2/2003 |
| WO | 2004/058715 | 7/2004 |
| WO | 2005/047296 | 5/2005 |
| WO | 2007/032498 | 3/2007 |
| WO | WO 2007/032498 * | 3/2007 |
| WO | 2008/129846 | 10/2008 |
| WO | 2008/156159 | 12/2008 |
| WO | 2010/021093 | 2/2010 |
| WO | WO 2010/021093 A1 * | 2/2010 |
| WO | 2010/071164 | 6/2010 |

OTHER PUBLICATIONS

U.S. Appl. No. 13/157,590, filed Jun. 10, 2011, Koji Sato.
U.S. Appl. No. 13/162,922, filed Jun. 17, 2011, Takeo Koyama.
U.S. Appl. No. 13/163,287, filed Jun. 17, 2011, Takashi Abiko.
U.S. Appl. No. 13/181,596, filed Jul. 13, 2011, Makoto Ono.
U.S. Appl. No. 13/273,360, filed Oct. 14, 2011, Toshiharu Yoshino.
U.S. Appl. No. 13/328,847, filed Dec. 16, 2011, Makoto Kamada.
U.S. Appl. No. 13/554,610, filed Jul. 20, 2012, Tetsuya Kimura.
U.S. Appl. No. 13/622,783, filed Sep. 19, 2012, Tetsuya Suzuki.
U.S. Appl. No. 13/231,081, filed Sep. 2, 2011, Koutarou Kawanami.
U.S. Appl. No. 13/228,928, filed Sep. 9, 2011, Takeo Koyama.
Escolar et al. "Edoxaban tosilate: Direct factor Xa inhibitor prevention of post operative venous thromboembolism treatment of atrial fibrillation" Drugs of the Future, 34(11), p. 861-872, 2009, Abstract only.
International Preliminary Report on Patentability, issued in PCT/JP2009/070613, mailed Jul. 5, 2011.
International Search Report, issued in PCT/JP20091070613, mailed Feb. 16, 2010.
Written Opinion of the International Searching Authority, issued in PCT/JP2009/070613, mailed Jul. 5, 2011.
International Preliminary Report on Patentability, issued in PCT/JP2009/070874, mailed Jul. 5, 2011.
International Search Report, issued in PCT/JP20091070874, mailed Mar. 23, 2010.
Written Opinion of the International Searching Authority, issued in PCT/JP2009/070874, mailed Jul. 5, 2011.
International Preliminary Report on Patentability, issued in PCT/JP2009/071016, mailed Jul. 5, 2011.
International Search Report, issued in PCT/JP20091071016, mailed Feb. 16, 2010.
Written Opinion of the International Searching Authority, issued in PCT/JP2009/071016, mailed Jul. 5, 2011.
International Preliminary Report on Patentability, issued in PCT/JP2010/050128, mailed Aug. 16, 2011.
International Search Report, issued in PCT/JP2010/050128, mailed Apr. 6, 2010.
Written Opinion of the International Searching Authority, issued in PCT/JP2010/050128, mailed Aug. 16, 2011.
International Preliminary Report on Patentability, issued in PCT/JP2010/057990, mailed Dec. 12, 2011.
International Search Report, issued in PCT/JP2010/057990, mailed Jun. 8, 2010.
Written Opinion of the International Searching Authority, issued in PCT/JP2010/057990, mailed Dec. 12, 2011.
International Preliminary Report on Patentability, issued in PCT/JP2010/060261, mailed Dec. 20, 2011.
International Search Report, issued in PCT/JP2010/060261, mailed Sep. 21, 2010.
Written Opinion of the International Searching Authority, issued in PCT/JP2010/060261, mailed Dec. 20, 2011.
PCT International Preliminary Report on Patentability of Int'l App. No. PCT/JP2010/053905 dated Oct. 18, 2011, 5 pages.
International Search Report of Int'l App. No. PCT/JP2010/053905 dated Apr. 21, 2010, 2 pages.
English Translation of PCT Written Opinion of the International Searching Authority of Int'l App. No. PCT/JP2010/053905 dated May 11, 2010, 4 pages.
PCT International Preliminary Report on Patentability of Int'l App. No. PCT/JP2010/053976 dated Oct. 18, 2011, 5 pages.
International Search Report of Int'l App. No. PCT/JP2010/053976 dated Apr. 13, 2010, 2 pages.
English Translation of PCT Written Opinion of the International Searching Authority of Int'l App. No. PCT/JP2010/053976 dated Apr. 13, 2010, 4 pages.
Patani, et al., "Bioisosterism: A rational approach in drug design", Chem. Rev. 1996, 3147-3176.
International Search Report of Int'l App. No. PCT/JP2011/065192 dated Jan. 5, 2012.
Written Opinion of the International Search Authority of Int'l App. No. PCT/JP2011/065192 dated Feb. 6, 2013.
International Preliminary Report on Patentability Chapter I (IB/373) of Int'l App. No. PCT/JP2011/065192 dated Feb. 12, 2013.
Office of Generic Drugs, "Scoring Configuration of Generic Drug Products", dated Nov. 1, 1995; www.fda.gov/downloads/AboutFDA/CentersOffices/CDER/ManualofPoliiesProcedures/ucm079779.pdf; accessed Sep. 6, 2012; cited in related U.S. Appl. No. 13/163,287.
Supplemental European Search Report mailed Jun. 4, 2012 in EP Application No. 09 83 3467, which corresponds to related U.S. Appl. No. 13/163,287.
Morrison, K. "Physical Science Level 3", Pearson Education: Capetown, pp. 16-18 (2008); cited in related U.S. Appl. No. 13/231,081.
International Search Report, issued on May 24, 2011 in PCT/JP2011/055955, which corresponds to related U.S. Appl. No. 13/622,783.
International Preliminary Report on Patentability & Written Opinion by the International Searching Authority, issued on May 24, 2011 in PCT/JP2011/055955, which corresponds to related U.S. Appl. No. 13/622,783.
International Search Report, issued on Feb. 19, 2013 in PCT/JP2012/082279, which corresponds to related U.S. Appl. No. 13/554,610.
U.S. Appl. No. 13/740,026, filed Jan. 13, 2013, Takashi Abiko.
U.S. Appl. No. 14/041,681, filed Sep. 30, 2013, Tetsuya Kimura
Escolar, G., et al., "Edoxaban tosilate" Drugs of the Future, 34(11), 861-872, (2009).
De La Mode et al. "Effect of Renal Function on Edoxaban Pharamacokinetics (PK) and on population PK/PK-PD model" Journal of Clinical Pharmacology, 49(9), p. 1124, 2009, abstract only.
Instruction Manual of the Japanese Pharmacopoeia, 15th et, 2006, B-211 to B-217.
Weitz, J. I. et al. (2010). "Randomised, parallel-group, multicentre, multinational phase 2 study comparing edoxaban, an oral factor Xa

(56) References Cited

OTHER PUBLICATIONS inhibitor, with warfarin for stroke prevention in patients with atrial fibrillation". Thrombosis and Haemostasis 104 (3): 633-641.

Ruff C.T. et al. "Evaluation of the novel factor Xa inhibitor edoxaban compared with warfarin in patients with atrial fibrillation: Design and rationale for the Effective aNticoaGulation with factor xA next GEneration in Atrial Fibrillation—Thrombolysis in Myocardial Infarction study 48 (ENGAGE AF—TIMI 48)" Am. Heart J. Oct. 2010; 160 (4): 635-41.

Lixiana (registered trademark) tablets, package insert, the 2nd revised edition in Jul. 2011.

Homepage of information on ethical pharmaceuticals review (http://www.info.pmda.go.jp/approvalSrch/PharmacySrchInit?), Pharmaceuticals and Medical Devices Agency, LIXIANA (registered trademark) tablets, The Brief Summary of Application Material, 2.7.6 Summary of Individual Studies, 114-128, (2011).

Homepage of information on ethical pharmaceuticals review (http://www.info.pmda.go.jp/approvalSrch/PharmacySrchInit?), Pharmaceuticals and Medical Devices Agency, LIXIANA (registered trademark) tablets, The Brief Summary of Application Material, 2.5 Global Assessment for Clinical Practice 48-76, (2011).

Homepage of information on ethical pharmaceuticals review (http://www.info.pmda.go.jp/approvalSrch/PharmacySrchInit?), Pharmaceuticals and Medical Devices Agency, LIXIANA (registered trademark) tablets, The Brief Summary of Application Material, 2.7.2 Clinical Pharmacological Study, 30-32 Section "2.3.2 PK for Renal Functional Impairment in Europe", (2011).

Assessment Report as of Feb. 9, 2011 for LIXIANA (registered trademark) tablets, 41-43 Section "(2) Validity of Reduced Dose for Renal Functional Impairment Patient and for combined use with P-gp inhibitor".

Assessment Report as of Feb. 9, 2011 for LIXIANA (registered trademark) tablets, 66-69 Section "(7)1 Individual with Renal Functional Impairment".

Assessment Report as of Feb. 9, 2011 for LIXIANA (registered trademark) tablets, 74-78.

Ogawa, S. et al. "Antithrombotic therapy in atrial fibrillation: evaluation and positioning of new oral anticoagulant agents", Circ. J., 2011, vol. 75, 1539-1547.

Serajuddin, Abu T.M. "Salt formation to improve drug solubility", Advanced Drug Delivery Reviews 59 (2007), 603-616.

Dubois, D., et al., "Clinical calorimetry. X. A formula to estimate the approximate surface area if the height and weight be known" Archives of Internal Medicine, 17, 863-71 (1916).

Elodi, S., et al., "Optimization of conditions for the catalytic effect of the factor IXa-factor VIII complex: probable role of the complex in the amplification of blood coagulation" Thrombosis Research, 15(5-6), 617-29 (1979).

Fujimoto, et al., "Studies on the physical surface area of Japanese: Part 18 calculation formulas in three stages over all age" Japanese Journal of Hygene, vol. 23(5): 443-450 (1968)—(Contains an English Abstract).

Furugohri, T., et al., "DU-176b, A potent and orally active factor Xa inhibitor: In vitro and in vivo pharmacological profiles" Journal of Thrombosis and Haemostasis, 6(9), 1542-1549 (2008).

Goldberg, Si, et al., "Correlation of configuration and rotatory direction for several 4-substituted cyclohexenes" Journal of Organic Chemistry, 31:240-243 (1966).

Hylek, E.M., "Drug evaluation: DU-176b, an oral, direct Factor Xa antagonist." Current Opinion in Investigational Drugs, 8, (9), 778-783 (2007).

Johansson, LC, et al., "Comparison of the Pharmacokinetics and Pharacodynamics of Ximelagatran in young and elderly, healthy Japanese men" Blood 100, 3980 (2002).

Mendell, J., et al., "The pharmacokinetics and pharmacodynamics of the direct factor Xa inhibitor, edoxaban co-administered with digoxin: a randomized, open-label, dual treatment sequence, parallel-group study" Journal of Clinical Pharmacology, 49(9), 1125 (2009).

Mendell, J., et al., "Thorough QT/QTC study with edoxaban to evaluate effect of therapeutic and supratherapeutic exposure on QTC interval duration in healthy subjects" Journal of Clinical pharmacology 49(9), 1122 (2009).

Mould, D., et al., "A population pharmacokinetic pharmacodynamic and logistic regression analysis of lotrafiban in patients" Clinical Pharmacology and Therapeutics 69(4), 210-222 (2001).

Mueck, W., et al. "Population pharmacokinetics and pharmacodynamic of rivaroxaban—an oral, direct factor Xa inhibitor—in patients undergoing major orthopaedic surgery" Clinical Pharmacokinetics, 47(3), 203-216 (2008).

Nohira, H. "4 Diastereomer Method", Edited by CSJ: The Chemical Society of Japan, kogaku Iseitai no Bunri Kikan Kagaku Sosetsu No. 6, 3rd edition, Japan Scientific Societies Press, pp. 45 to 54, (1999).

Product Information, Clexane ® and Clexane ® Forte, Clexane ® PI MKT, #6178v16, pp. 1-19 (2008).

Ridout, G., et al., "Effect of renal function on edoxaban pharmacokinetics (PK) and on population PK/PK-PD model" Journal of Clinical Pharmcology 49(9), 1124 (2009).

Schwartz, HM, et al., "Predicting the Enantiomeric Selectivity of Chymotrypsin. Homologous Series of Ester Substrates" J. Am. Chem. Soc., 100, 5199-5203, (1978).

Sixma JJ, et al., "The ideal anti-thrombotic drug" Thrombosis research, 68(6), 507-12 (1992).

Takahashi, H. "3.Warfarin Oto no kojinsa" Kessen to Junkan, 14(3), 198-202 (2006) (English Translation Provided).

Tanyeli, C, et al., "Enzyme catalyzed reverse enantiomeric separation of methyl (±)-3-cyclohexene-1-carboxylate" Tetrahedron: Asymmetry, 15, 2057-2060, (2004).

Trost, BM, et al., "An Asymmetric Synthesis of (+)-Phyllanthoci" Tetrahedron Lett., 32, 1613-1616, (1991).

Vene, N., et al., "High D-dimer levels predict cardiovascular events in patients with chronic atrial fibrillation during oral anticoagulant therapy" Thrombosis and Haemostasis, 90(6), 1163-1172 (2003).

Kozma, D., "CRC Handbook of Optical Resolutions Via Diastereomeric Salt Formation", CRC Press: Washington, DC, Chapters 4, 5, and 6 (2002).

Murakami, "Asymmetric Transformation of a Racemic a-(Phthalimidooxy)arylacetic Ester by a Combination of Preferential Crystallization and Simultaneous Racemization" Chirality 5 141-48 (1993).

Allan, R., "Synthesis of analogs of GABA. VI. Stereoisomers of cis-3-aminocyclohexanecarboxylic acid" Australian Journal of Chemistry, 34(10):2231-36 (Abstract only), (1981).

Chiappe, et al. "Nucleophilic Displacement Reactions in Ionic Liquids: Substrate and Solvent Effect in the Reaction of NaN3 and KCN with Alkyl Halides and Tosylates," Journal of Organic Chemistry 68:6710-15 (2003).

Betti, C., et al. "Reactivity of anionic nucleophiles in ionic liquids and molecular solvents," Tetrahedron 64:1689 (2008).

Blagden, N., et al. "Crystal engineering of active pharmaceutical ingredients to improve solubility and dissolution rates." Advanced Drug Delivery Reviews, 59:603-616 (2007).

Serajuddin, A., "Salt formation to improve drug solubility." Advanced Drug Delivery Reviews, 59:617-630 (2007).

Ohta, T., et al. "Preparation of N,N'-bis(heterocyclic acyl)cycloalkanediamine and heterocyclediamine derivatives as inhibitors of activated blood coagulation factor X (factor Xa)", Hcaplus 2003:5928 (2003).

Furugohri, T, et al, "Pharmaceutical Characterization, Antithromboti and Bleeding Effects of DU-176b", Journal of Thrombosis and Haemostasis, 3(supp. 1), Abstract P1110, (2005).

Zafar, UM, et al., "Antithrombotic effects of factor Xa inhibition with DU-176b: Phase-I study of an oral, direct factor Xa inhibitor using an ex-vivo flow chamber", Thrombosis and Haemostasis, 98(4):833-888 (2007).

Walker, MB, "Understanding the PT-INR Test", obtained from the internet www.vclotacare.com/ptinr.aspx (retrieved Apr. 24, 2012).

(56) References Cited

OTHER PUBLICATIONS

Anonymous, "A phase 2, randomized, parallel group, multi-center, multi-national study for the evaluation of safety and efficacy of two fixed dosages of DU-176b in subjects with non-valvular atrial fibrillation", Clinical Trials.gov NCT00806624 obtained from the internet clinicaltrials.gov/archive/NCT00806624/2008_12_10 (retrieved Apr. 23, 2012).

Hyers, T. M., et al, "Management of Venous Thromboembolism", Arch Intern Med., 163:759-768 (2003).

Turpie, Agg., "Oral, direct factor Xa inhibitors in development for the prevention and treatment of thromboembolic diseases", Arteriosclerosis, Thrombosis, and Vascular Biology, 27:1238-1247 (2007).

De Caterina, R, et al. "Anticoagulants in heart disease: current status and perspectives", European Heart Journal 28:880-913 (2007).

Dyke, CK., "First experience with direct factor Xa inhibition in patients with stable coronary disease: a pharmacokinetic and pharmacodynamics evaluation", Circulation., 105:2385-2391 (2002).

Iba, T., et al., "Factor Xa-inhibitor (DX-9065a) modulates the leukocyte-endothelial cell interaction in endotoxemic rat", Shock., 17(2):159-162 (2002).

* cited by examiner

PROCESS FOR PREPARATION OF OPTICALLY ACTIVE DIAMINE DERIVATIVE SALT

This application is a continuation of International Application No. PCT/JP2011/065192, filed on Jul. 1, 2011, entitled "PROCESS FOR PREPARATION OF OPTICALLY ACTIVE DIAMINE DERIVATIVE SALT", which claims the benefit of Japanese Patent Application Number JP 2010-151922, filed on Jul. 2, 2010, both of which are hereby incorporated by reference.

FIELD OF THE INVENTION

The present invention relates to a process for the industrial preparation of an optically active diamine derivative that is important for the production of a compound represented by formula (X) as an activated blood coagulation factor X (FXa) inhibitor or a pharmacologically acceptable salt thereof, or a hydrate thereof.

BACKGROUND

A compound represented by the following formula (X) [hereinafter, also referred to as compound (X)] or a pharmacologically acceptable salt thereof, or a hydrate thereof is a compound that exhibits an FXa inhibitory effect, as disclosed in Patent Literatures 1 to 3, and is useful as a preventive and/or therapeutic drug for thrombotic and/or embolic diseases:

[Formula 1]

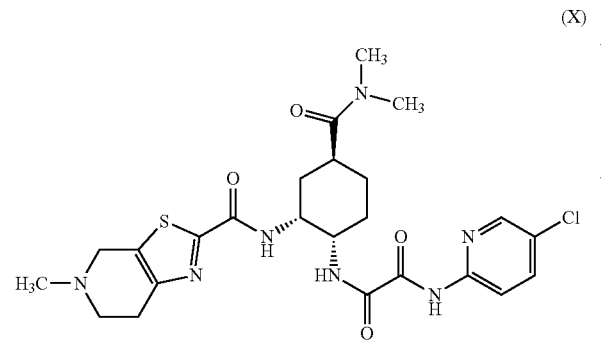

(X)

The pamphlet of International Publication No. WO 2007/032498 discloses a process for preparing an FXa inhibitor compound (X) or a pharmacologically acceptable salt thereof, or a hydrate thereof. The process for producing compound (X) disclosed therein involves, as shown in [Scheme A] below, azidifying compound (2) to produce azide compound (3), subsequently reducing compound (3) into amino compound (1a), subsequently treating compound (1a) with anhydrous oxalic acid to obtain compound (1), which is then treated with compound (4) (ethyl 2-[(5-chloropyridin-2-yl)amino]-2-oxoacetate monohydrochloride) in the presence of a base to produce compound (5), followed by several steps from compound (5). This pamphlet also discloses crystals of the oxalate of compound (1) as a production intermediate.

[Scheme A]

[Formula 2]

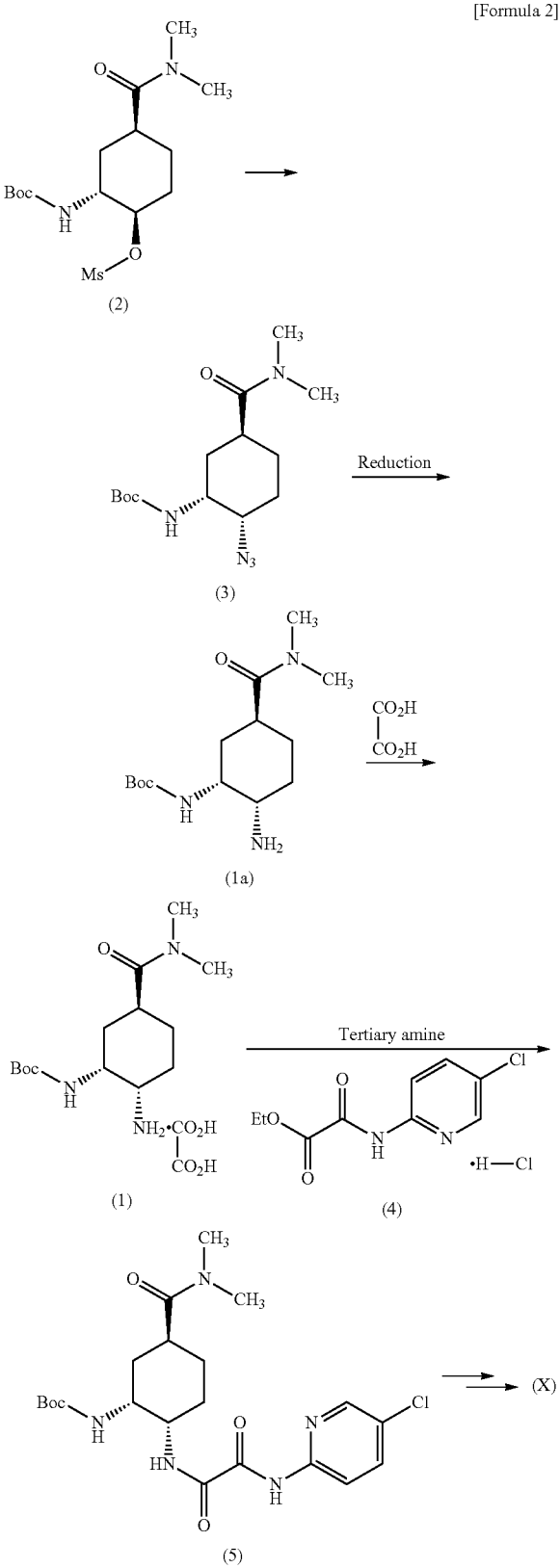

wherein Boc represents a tert-butoxycarbonyl group.

CITATION LIST

Patent Literatures

Patent Literature 1: International Publication No. WO 2004/058715
Patent Literature 2: International Publication No. WO 2003/016302
Patent Literature 3: International Publication No. WO 2003/000680
Patent Literature 4: International Publication No. WO 2007/032498

SUMMARY OF THE INVENTION

Technical Problem

The present inventors have conducted diligent studies on efficient methods for producing FXa inhibitor compound (X) or a pharmacologically acceptable salt thereof, or a hydrate thereof. Compound (1) is an important intermediate for the production of FXa inhibitor compound (X) or a pharmacologically acceptable salt thereof, or a hydrate thereof. An important challenge is to produce compound (1) at high yields with high purity.

As a result of conducting studies on a process for the preparation of compound (1), the present inventors have found the following three new problems (a) to (c) to be solved:

(a): Anhydrous state of compound (1): it is important to carry out, under anhydrous conditions, the step of producing compound (5) (oxalic acid diamide derivative) from compound (1) in the scheme described above, for obtaining compound (5) as a product at high yields. Therefore, one problem to be solved is to maintain the anhydrous state of compound (1), because use of compound (1) in a hydrous form containing attached water or in the form of hydrate crystals significantly reduces the yields of compound (5);

(b): Purity of compound (1) (cis-diamino derivative): the production of azide compound (3) from compound (2) forms compound (3) in the cis-form of interest as well as its related trans-isomer compound (3-trans) (see the pamphlet of International Publication No. WO 2001/74774). Thus, amino compound (1a), which is obtained by the reduction of the crude azide compound, also includes the same percentage as above of the trans-isomer derived from the azidification step. Therefore, a further problem to be solved is to remove this trans-isomer compound (1a-trans); and (c): another problem to be solved is to provide a preparation process that can be carried out on an industrial scale in terms of reaction yields, operability, etc.

A possible solution to problem (b) is purification by crystallization. The pamphlet of International Publication No. WO 2007/032498 discloses that a crystalline compound represented by formula (1) was obtained from amino compound (1a) and anhydrous oxalic acid. This production method, however, has been shown to present the following new problems (d) to (h) to be solved:

(d): in the process for the preparation of compound (1) disclosed in the pamphlet of International Publication No. WO 2007/032498, the precipitation of an amorphous portion was observed in proximity to areas that had undergone the dropwise addition of an anhydrous oxalic acid solution, demonstrating that crystallization proceeded gradually by way of an amorphous portion. Thus, this crystallization requires a long time, and the formation of an amorphous portion makes stirring difficult;

(e): it was demonstrated that crystal polymorphs were precipitated depending on the time over which the anhydrous oxalic acid solution was added dropwise. Thus, the production process is not stable. In addition, crystallization in a single crystal form requires a long time until its completion, due to the crystal polymorphs;

(f): incomplete crystallization associated with (e) involves an amorphous portion, which in turn reduces operability to the extent that filtration procedures are impossible to achieve;

(g): it was demonstrated that stirring for a long time initiated the precipitation of crystals of the related trans-isomer compound (1-trans) present in the stirred solution due to supersaturation. Contamination with this compound (1-trans) reduces the purity of the cis-diamino derivative compound (1); and (h): contamination with the trans-isomer compound (1-trans) may be prevented to some extent by control of the stirring time or temperature or by changing the crystallization solvent or increasing the amount of solvent. Such increase in the amount of solvent, however, is not preferable because it entails upsizing the production apparatus. In addition, the occurrence of re-contamination with compound (1-trans) attributed to a longer stirring time was observed, showing underlying problems for a robust industrial production method.

Thus, the present inventors have found a new challenge to find a fundamental crystallization method capable of solving these new problems and produce highly pure anhydrous crystals represented by formula (1).

As a result of conducting studies on crystals of compound (1), the present inventors have discovered that cis-derivative compound (1) and its trans-isomer compound (1-trans) include several types of crystal polymorphs: anhydrous crystals and hydrous crystals. The present inventors have found that, among these, monohydrate crystals represented by formula (1b) and their trans-isomer monohydrate crystals represented by formula (1b-trans) differ largely as regards their solubility in water, and that the monohydrate crystals represented by formula (1b-trans) are highly water-soluble. Thus, the present inventors have found that monohydrate crystals of the desired cis-diamino derivative represented by formula (1b) can be produced with high purity and high selectivity by utilizing the difference in water solubility between the monohydrate crystals represented by formula (1b) and the monohydrate crystals of formula (1b-trans), i.e., by adding water to the crystallization solvent. The present inventors have further found a novel crystal transformation process for the preparation of anhydrous crystals represented by formula (1) from the monohydrate crystals of the cis-diamino derivative represented by formula (1b). Based on these findings, the present invention has been completed.

[Formula 3]

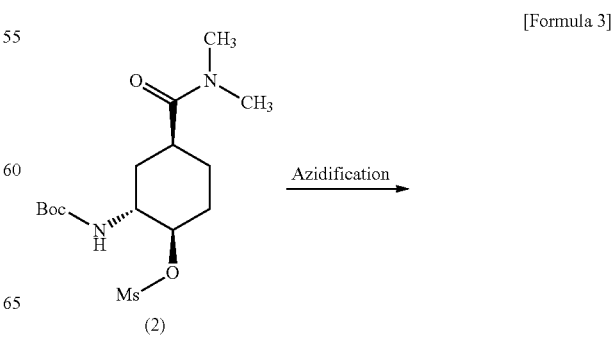

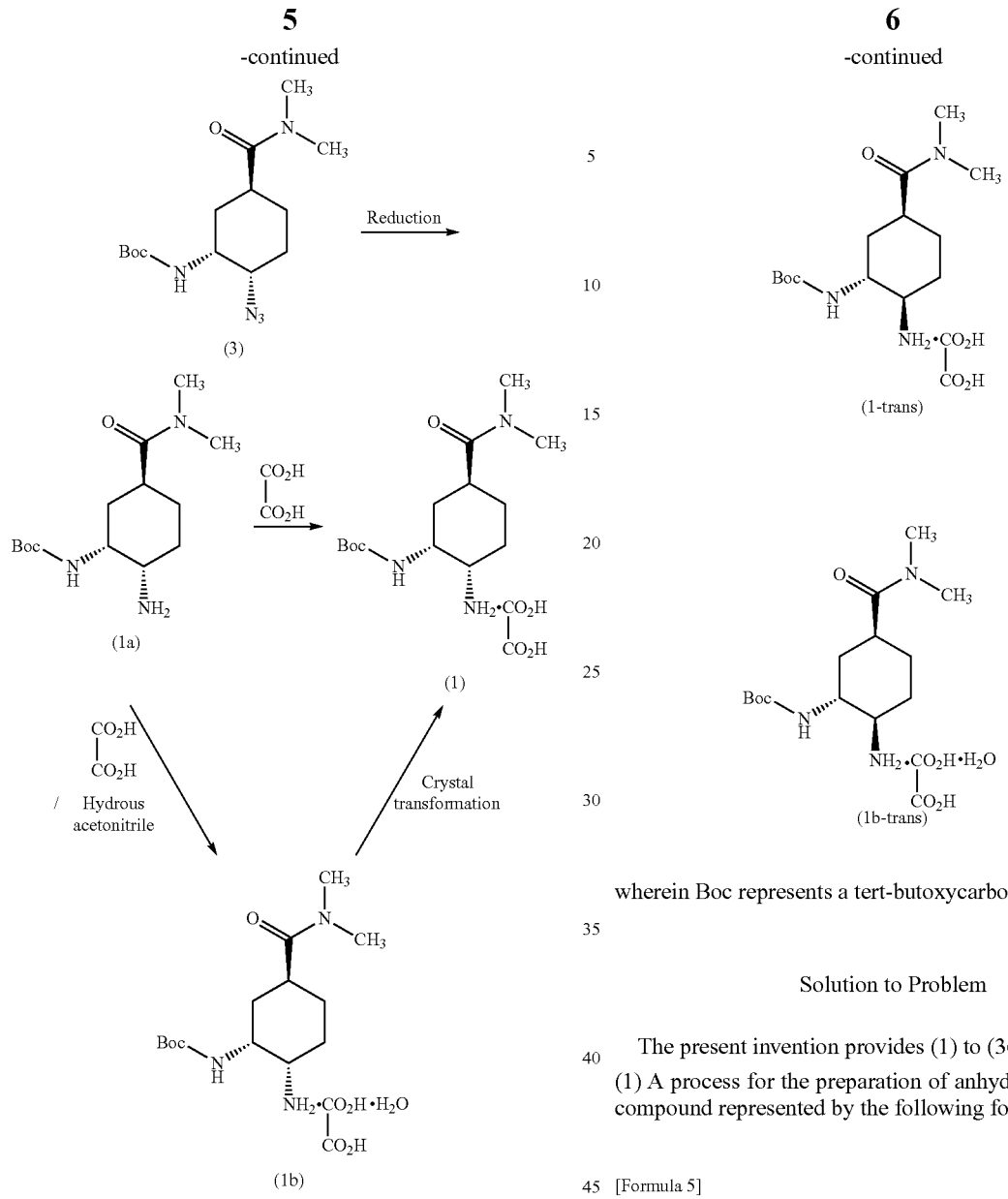

wherein Ms represents a methanesulfonyl group; and Boc represents a tert-butoxycarbonyl group.

[Formula 4]

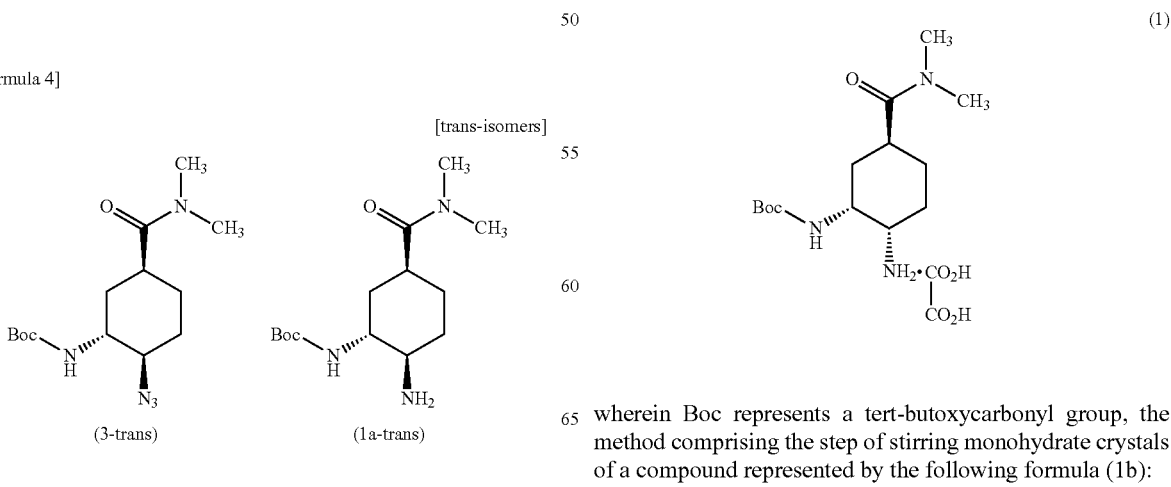

wherein Boc represents a tert-butoxycarbonyl group.

Solution to Problem

The present invention provides (1) to (36) shown below.

(1) A process for the preparation of anhydrous crystals of a compound represented by the following formula (1):

[Formula 5]

wherein Boc represents a tert-butoxycarbonyl group, the method comprising the step of stirring monohydrate crystals of a compound represented by the following formula (1b):

[Formula 6]

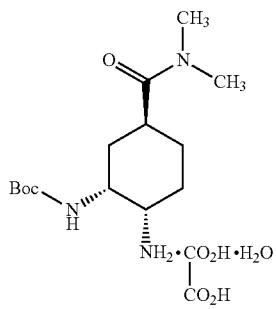
(1b)

wherein Boc is as defined above, in an organic solvent with a water content of less than 1% by weight under heating.

(2) A process for the preparation of anhydrous crystals of a compound represented by the following formula (1):

[Formula 7]

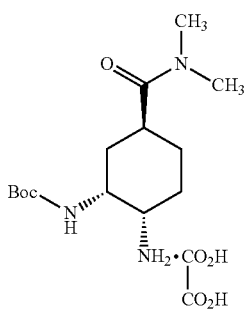
(1)

wherein Boc represents a tert-butoxycarbonyl group, the method comprising the steps of:

treating a compound represented by the following formula (1a):

[Formula 8]

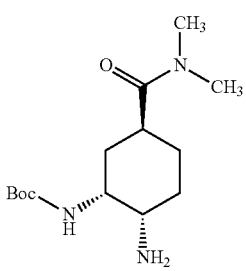
(1a)

wherein Boc is as defined above, with anhydrous oxalic acid in a hydrous organic solvent to obtain monohydrate crystals of a compound represented by the following formula (1b):

[Formula 9]

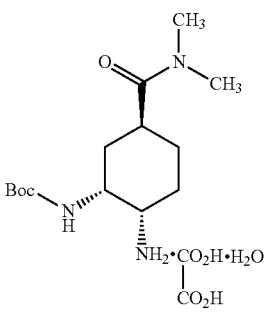
(1b)

wherein Boc is as defined above; and stirring the monohydrate crystals of the compound represented by formula (1b) in an organic solvent with a water content of less than 1% by weight under heating.

(2a) A process for the preparation of anhydrous crystals of a compound represented by the following formula (1):

[Formula 10]

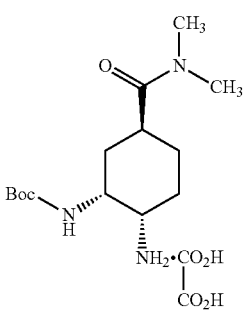
(1)

wherein Boc represents a tert-butoxycarbonyl group, the method comprising the steps of:

treating a compound represented by the following formula (2):

[Formula 11]

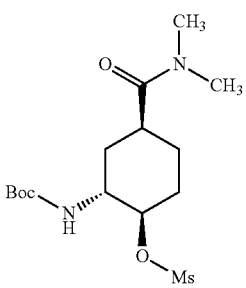
(2)

wherein Ms represents a methanesulfonyl group; and Boc is as defined above, with an azidification reagent in a solvent to obtain a compound represented by the following formula (3):

[Formula 12]

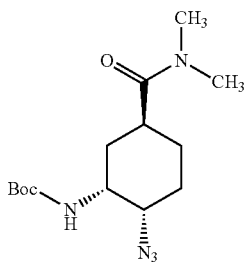
(3)

wherein Boc is as defined above;
reducing the compound represented by formula (3) to obtain a compound represented by the following formula (1a):

[Formula 13]

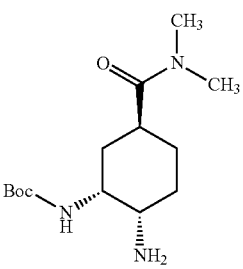
(1a)

wherein Boc is as defined above;
treating the compound represented by formula (1a) with anhydrous oxalic acid in a hydrous organic solvent to obtain monohydrate crystals of a compound represented by the following formula (1b):

[Formula 14]

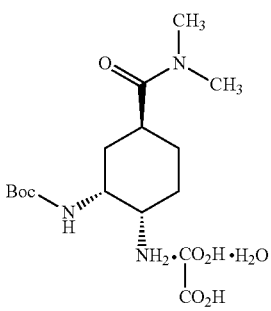
(1b)

wherein Boc is as defined above; and
stirring the monohydrate crystals of the compound represented by formula (1b) in an organic solvent with a water content of less than 1% by weight under heating.
(3) The preparation process according to (1) or (2), wherein the heating is performed at 50 to 80° C.
(4) The preparation process according to (1) or (2), wherein the heating is performed at 70 to 75° C.
(5) The preparation process according to any one of (1) to (4), wherein the stirring step further comprises distilling off the organic solvent by ½ to 4/7 of the total volume of the organic solvent under reduced pressure in the range of 40 to 75° C. and then re-adding an organic solvent in an amount corresponding to the amount distilled off.
(6) The preparation process according to (5), wherein the water content of the organic solvent is kept at less than 0.2% by weight in the distilling off of the organic solvent under reduced pressure and the re-addition.
(7) A process for the preparation of monohydrate crystals of a highly pure compound represented by the following formula (1b):

[Formula 15]

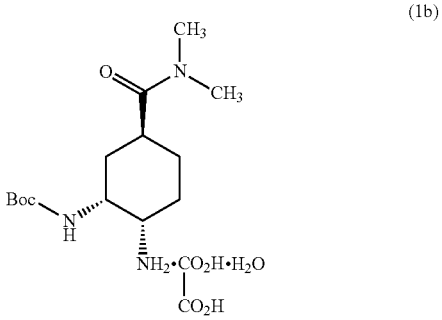
(1b)

wherein Boc represents a tert-butoxycarbonyl group,
the method comprising treating a compound represented by the following formula (1a):

[Formula 16]

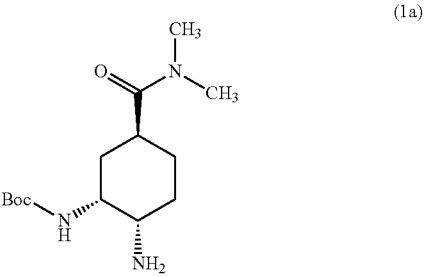
(1a)

wherein Boc is as defined above,
with anhydrous oxalic acid in a hydrous organic solvent.
(8) The process for the preparation of production method according to any one of (2) to (7), wherein the hydrous organic solvent is a hydrous organic solvent containing 4% or more water.
(9) The preparation process according to any one of (2) to (7), wherein the hydrous organic solvent is a hydrous organic solvent containing 4 to 10% water.
(10) The preparation process according to any one of (2) to (9), wherein the treatment with anhydrous oxalic acid comprises adding dropwise a solution of anhydrous oxalic acid in an organic solvent.
(11) The preparation process according to (10), wherein the dropwise addition is performed at 50 to 80° C.
(12) The preparation process according to (11), wherein after completion of the dropwise addition, the reaction mixture is further stirred at 50 to 80° C. for 2 to 5 hours.
(13) The preparation process according to any one of (1) to (12), wherein the organic solvent is one or two or more solvents selected from the group consisting of C1-C5 alkyl acetate solvents, linear or branched C1-C8 alcohol solvents, C1-C6 ketone solvents, toluene solvents, and C2-C5 nitrile solvents.

(14) The preparation process according to any one of (1) to (12), wherein the organic solvent is acetonitrile, toluene, or a mixed solvent of acetonitrile and toluene.

(15) The preparation process according to any one of (1) to (12), wherein the organic solvent is acetonitrile.

(16) A highly pure compound represented by formula (1b).

(17) The compound according to (16), wherein the compound is in the form of monohydrate crystals.

(18) The preparation process according to (7), wherein the compound represented by formula (1b) has a purity of 97.0% or more.

(19) The preparation process according to (7), wherein the compound represented by formula (1b) has a purity of 99.0% or more.

(20) A highly pure compound represented by formula (1).

(21) The compound according to (20), wherein the compound is in the form of anhydrous crystals.

(22) The preparation process according to (1) or (2), wherein the compound represented by formula (1) has a purity of 97.0% or more.

(23) The preparation process according to (1) or (2), wherein the compound represented by formula (1) has a purity of 99.0% or more.

(24) Form 2 anhydrous crystals of a compound represented by the following formula (1):

[Formula 17]

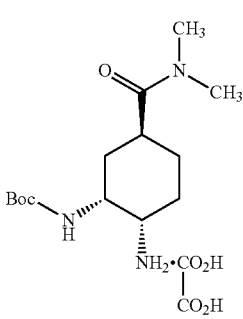

(1)

wherein Boc represents a tert-butoxycarbonyl group,
the crystals having characteristic peaks at diffraction angles (2θ) of 5.6 and 27.7° (±0.2°) in powder x-ray diffraction.

(25) The Form 2 anhydrous crystals of the compound represented by formula (1) according to (24), wherein the crystals exhibit the pattern shown in FIG. 2 in powder x-ray diffraction spectra.

(26) Form 2 monohydrate crystals of a compound represented by the following formula (1b):

[Formula 18]

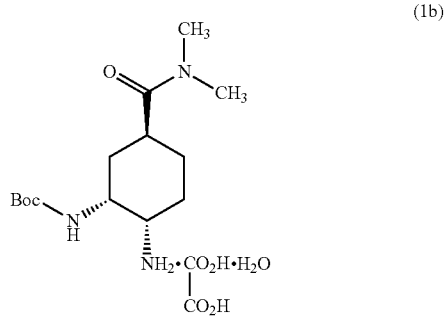

(1b)

wherein Boc is as defined above,
the crystals having characteristic peaks at diffraction angles (2θ) of 7.0 and 22.9° (±0.2°) in powder x-ray diffraction.

(27) The Form 2 monohydrate crystals of the compound represented by formula (1b) according to (26), wherein the crystals exhibit the pattern shown in FIG. 4 in powder x-ray diffraction spectra.

(28) Form 1 monohydrate crystals of a compound represented by the following formula (1b):

[Formula 19]

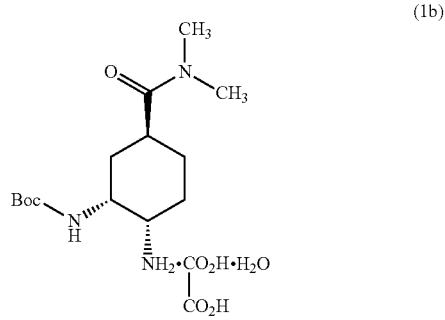

(1b)

wherein Boc is as defined above,
the crystals having characteristic peaks at diffraction angles (2θ) of 8.5 and 26.5° (±0.2°) in powder x-ray diffraction.

(29) The Form 1 monohydrate crystals of the compound represented by formula (1b) according to (28), wherein the crystals exhibit the pattern shown in FIG. 3 in powder x-ray diffraction spectra.

(30) A process for the preparation of a compound represented by the following formula (X-a):

[Formula 20]

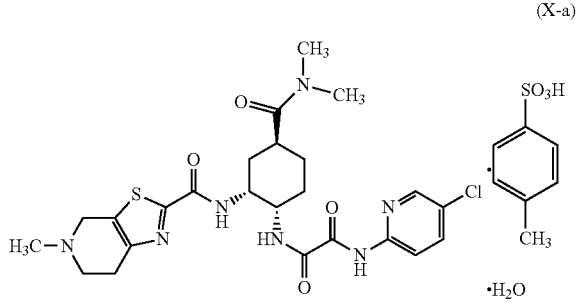

(X-a)

the method using anhydrous crystals of a compound represented by the following formula (1):

[Formula 21]

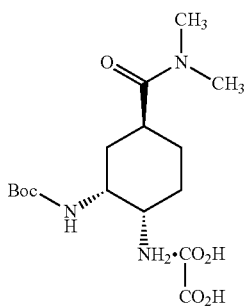
(1)

wherein Boc represents a tert-butoxycarbonyl group, the crystals being produced by a method according to (1).

(31) A process for the preparation of a compound represented by the following formula (X-a):

[Formula 22]

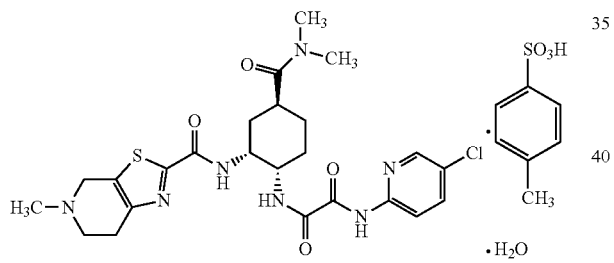
(X-a)

the method using anhydrous crystals of a compound represented by formula (1) produced by a method according to (1) and comprising the steps of:

treating anhydrous crystals represented by formula (1) with a compound represented by the following formula (4):

[Formula 23]

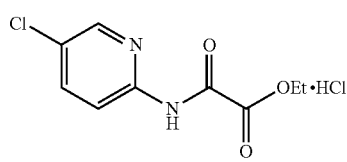
(4)

in the presence of a base to obtain a compound represented by the following formula (5):

[Formula 24]

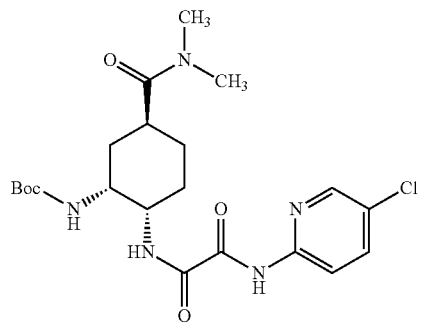
(5)

wherein Boc represents a tert-butoxycarbonyl group;

deprotecting the Boc group in the compound of formula (5) and then treating the resulting compound with a compound represented by the following formula (7):

[Formula 25]

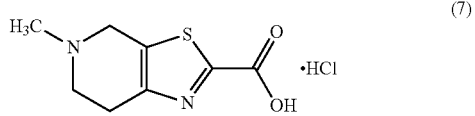
(7)

in the presence of a base to obtain a compound in the free form represented by the following formula (X):

[Formula 26]

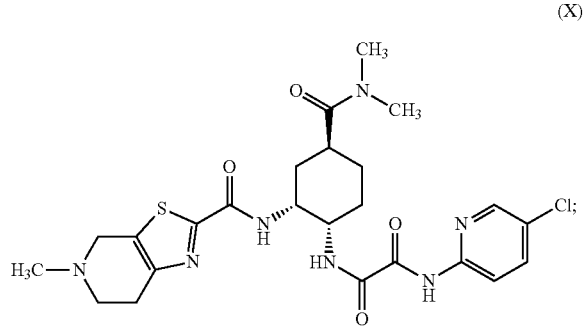
(X)

and treating the compound represented by formula (X) with p-toluenesulfonic acid or a hydrate thereof in a solvent to obtain a compound represented by formula (X-a).

(32) A highly pure compound represented by formula (X-a).

(33) The compound according to (32), wherein the compound has a purity of 99.50% by weight or more.

(34) The compound according to (32), wherein the compound has a purity of 99.75% by weight or more.

(35) The preparation process according to (30) or (31), wherein the compound represented by formula (X-a) has a purity of 99.50% by weight or more.

(36) The preparation process according to (30) or (31), wherein the compound represented by formula (X-a) has a purity of 99.75% by weight or more.

Advantageous Effects of Invention

According to the present invention, anhydrous crystals of a cis-diamino derivative represented by formula (1) that is an important intermediate for the production of FXa inhibitor (X) or a pharmacologically acceptable salt thereof, or a hydrate thereof can be produced with high purity. Thus, the preparation process of the present invention is useful as a process for producing FXa inhibitor (X) or a pharmacologically acceptable salt thereof, or a hydrate thereof.

DETAILED DESCRIPTION

Figure 1:
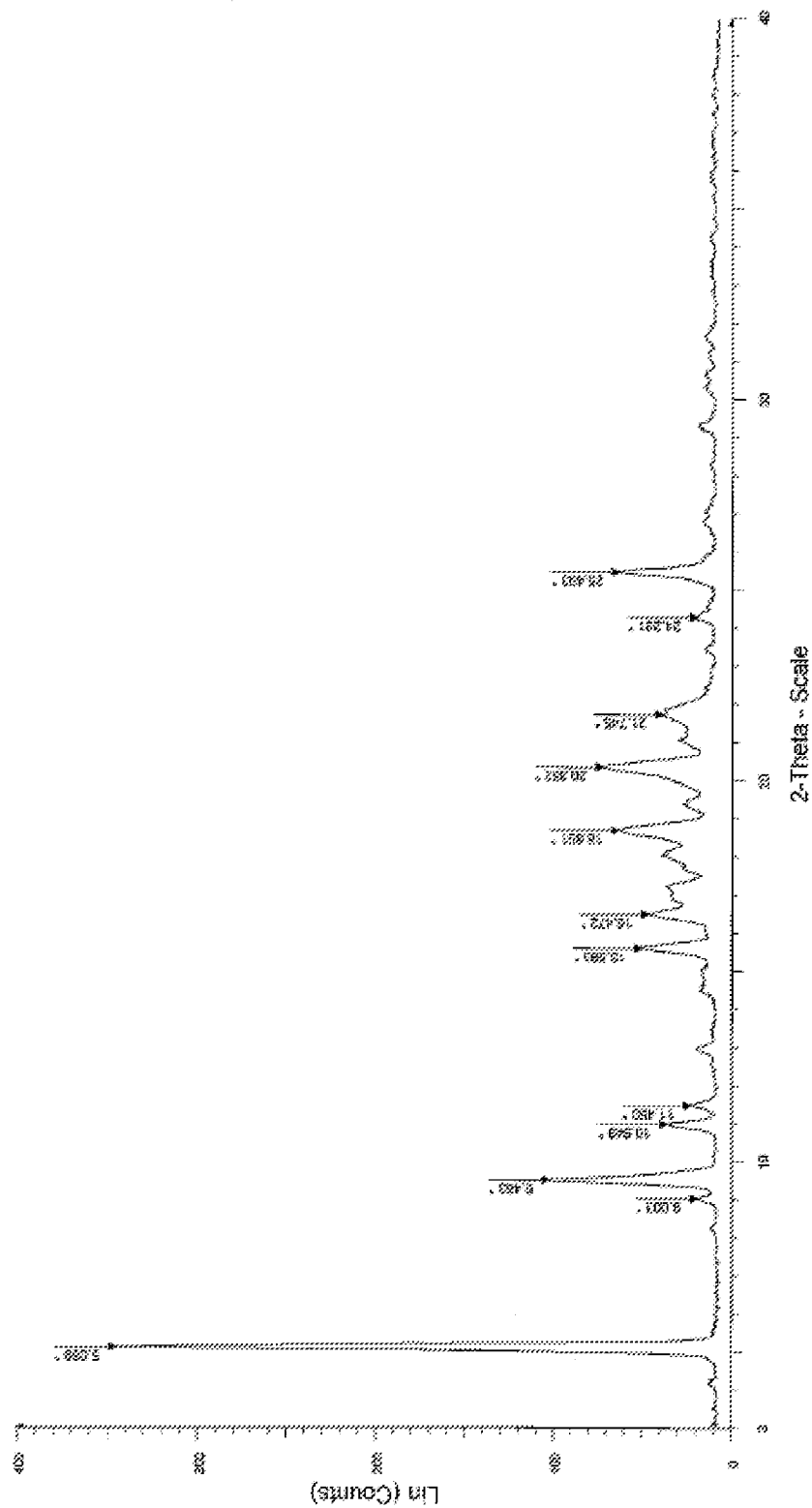
FIG. 1 shows a powder x-ray diffraction diagram of Form 1 anhydrous crystals of a compound represented by formula (1).

Hereinafter, the present invention will be described in detail.

The specific "FXa inhibitor" according to the present specification is preferably, for example, compound (X) described above. Compound (X) may be the free form (free base) or a hydrate thereof or may be a pharmacologically acceptable salt or a hydrate of the salt.

Examples of the pharmacologically acceptable salt of compound (X) can include hydrochloride, sulfate, hydrobromide, hydroiodide, phosphate, nitrate, benzoate, methanesulfonate, 2-hydroxyethanesulfonate, p-toluenesulfonate, acetate, propanoate, oxalate, malonate, succinate, glutarate, adipate, tartrate, maleate, fumarate, malate, and mandelate.

The salt of compound (X) is preferably hydrochloride or p-toluenesulfonate, particularly preferably p-toluenesulfonate.

Compound (X) or a salt thereof, or a hydrate thereof is preferably $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide;

$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide hydrochloride;

$N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide mono-p-toluenesulfonate; and $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide mono-p-toluenesulfonate monohydrate, particularly preferably $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide mono-p-toluenesulfonate monohydrate represented by the following formula (X-a):

[Formula 27]

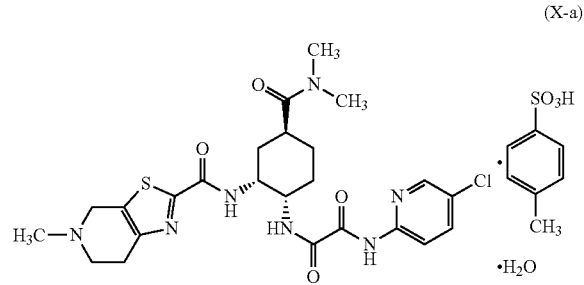

(X-a)

An amino compound represented by formula (1a) can be produced by a process described in the pamphlet of International Publication No. WO 2007/032498. Specifically, compound (1a) can be produced by producing compound (3) by the azidification of mesyloxy compound (2) and subsequently reducing azide compound (3).

[Formula 28]

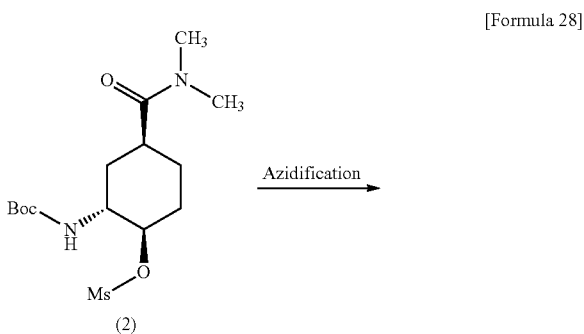

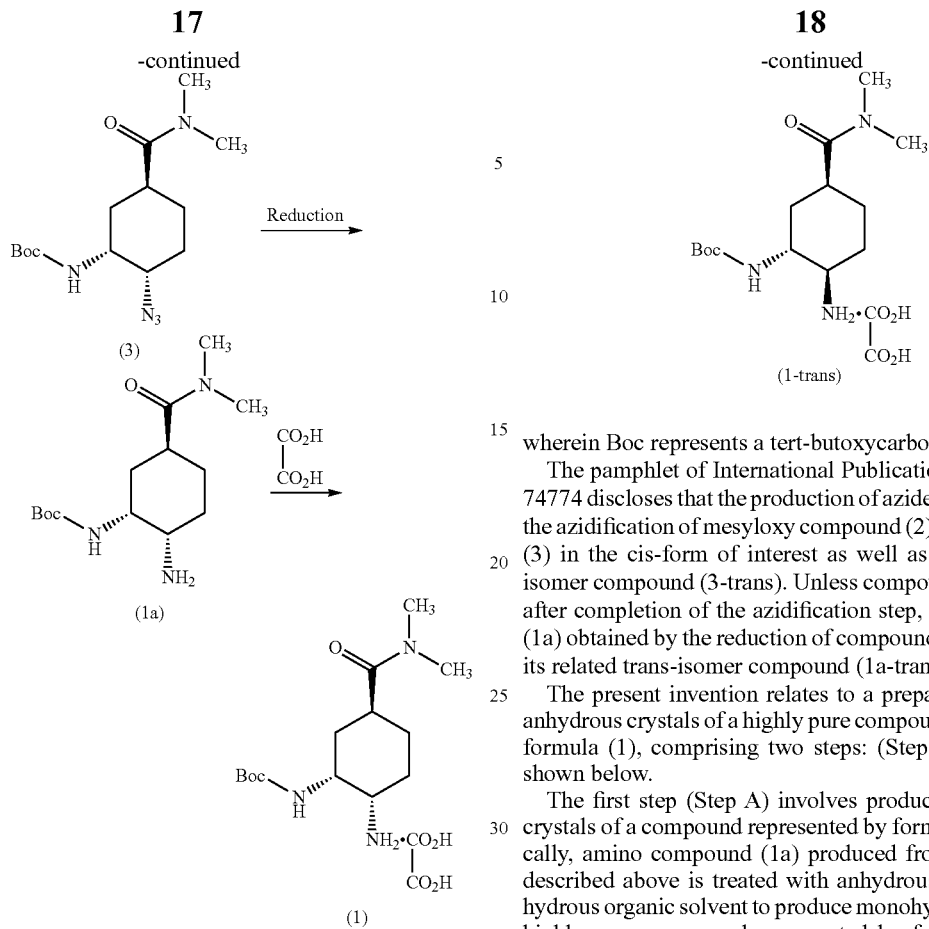

wherein Ms represents a methanesulfonyl group; and Boc represents a tert-butoxycarbonyl group.

In this context, it is known that the azidification step of this preparation process forms trans-isomer compound (3-trans) as a by-product, resulting in the contamination of compound (3), compound (1a) and its oxalate compound (1) with their related trans-isomer compounds (3-trans), (1a-trans), and (1-trans) shown below as by-products unless purification procedures are performed in any step (see the pamphlet of International Publication No. WO 2001/74774). In the production of an FXa inhibitor compound represented by formula (X) or a pharmacologically acceptable salt thereof, or a hydrate thereof, it is important to separate and remove these related compounds of the production intermediates, to improve the quality of the pharmaceutical compounds as final products. Also, the efficiency of this separation and removal is of great value to improving in the yield in bulk production.

[Formula 29] [trans-isomers]

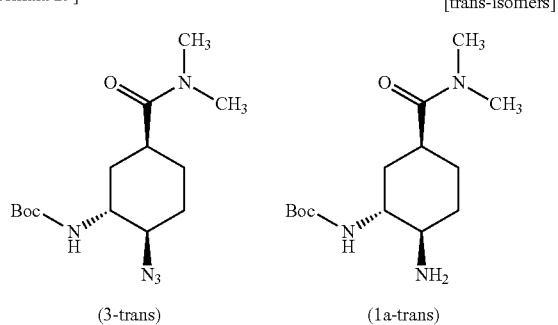

wherein Boc represents a tert-butoxycarbonyl group.

The pamphlet of International Publication No. WO 2001/74774 discloses that the production of azide compound (3) by the azidification of mesyloxy compound (2) forms compound (3) in the cis-form of interest as well as its related trans-isomer compound (3-trans). Unless compound (3) is purified after completion of the azidification step, amino compound (1a) obtained by the reduction of compound (3) also includes its related trans-isomer compound (1a-trans).

The present invention relates to a preparation process of anhydrous crystals of a highly pure compound represented by formula (1), comprising two steps: (Step A) and (Step B) shown below.

The first step (Step A) involves producing monohydrate crystals of a compound represented by formula (1b). Specifically, amino compound (1a) produced from compound (2) described above is treated with anhydrous oxalic acid in a hydrous organic solvent to produce monohydrate crystals of a highly pure compound represented by formula (1) with a reduced percentage content of its related compound.

(A-1): To compound (1a), an organic solvent and water are added in amounts that achieve a hydrous organic solvent containing 4% by volume or more of water to prepare a suspension or slurry.

(A-2): The suspension or slurry is heated to an internal temperature of 50 to 70° C. with stirring.

(A-3): A solution containing oxalic acid dissolved in an organic solvent is prepared and added dropwise into the solution of (A-2) over 1 to 2 hours in an internal temperature range of 50 to 70° C. to prepare a suspension or slurry.

(A-4): After completion of the dropwise addition, the reaction mixture is stirred for 2 to 5 hours in the range of 50 to 70° C.

(A-5): The reaction mixture is cooled to 20 to 40° C. with stirring.

(A-6): The precipitated crystals are collected by filtration, washed with an organic solvent, and then dried.

Hereinafter, respective preferable aspects of Steps (A-1) to (A-6) will be described.

The organic solvent in Step (A-1) may be a single organic solvent or a mixed solvent of organic solvents having water solubility. Examples thereof can include one solvent or a mixed solvent of two or more selected from C1-C5 alkyl acetate solvents, linear or branched C1-C8 alcohol solvents, C1-C6 ketone solvents, toluene solvents, and C2-C5 nitrile solvents. Examples of the C1-C5 alkyl acetate solvents can include methyl acetate, ethyl acetate, propyl acetate, isopropyl acetate, butyl acetate, and pentyl acetate. The linear or branched C1-C8 alcohol solvents may be linear or branched alcohols having 1 to 8 carbon atoms, and examples thereof can include methanol, ethanol, n-propanol, isopropanol, n-butanol, isobutanol, pentanol, hexanol, heptanol, and octanol. Examples of the C1-C6 ketone solvents can include acetone, methyl ethyl ketone, diethyl ketone, methyl isopropyl ketone, methyl isobutyl ketone, and cyclohexanone. Examples of the toluene solvents can include toluene and xylene. Examples of the C2-C5 nitrile solvents can include acetonitrile, propionitrile, and butyronitrile. These organic solvents may be used alone or as a mixture of two or more thereof. Since water is added in this step, the above organic solvent is preferably miscible with water. Among these organic solvents, acetonitrile and toluene are preferable. Acetonitrile is particularly preferable as a single organic solvent. The percentage water content of the hydrous organic solvent for production of hydrate crystals can be 4% by volume (v/v) or more and is preferably approximately 4 to 10% by volume (v/v), more preferably approximately 4 to 6% by volume (v/v). The total amount of the solvents used can be set to the range of 5 to 30 parts by volume (V/W), preferably the range of 7 to 15 parts by volume (V/W), with respect to 1 part of compound (1a).

The internal temperature in Step (A-2) is preferably in the range of 50 to 70° C., more preferably approximately 60±5° C. The mixture can be stirred in a suspension or slurry state.

Commercially available anhydrous oxalic acid may be used as the oxalic acid in Step (A-3). The amount of the anhydrous oxalic acid used is preferably 0.8 to 1 molar equivalents, more preferably 0.9 molar equivalents, with respect to compound (1a). The anhydrous oxalic acid is preferably added dropwise in the form of a solution. The solvent used in Step (A-1) may be used for the anhydrous oxalic acid solution, and acetonitrile is preferable. The amount of the solvent used in the anhydrous oxalic acid solution is preferably in the range of 2 to 5 parts by volume (2 to 5 V/W), more preferably approximately 3 parts by volume (3 V/W), with respect to 1 part of compound (1a). The temperature at which the anhydrous oxalic acid solution is added dropwise is preferably raised to improve the operability of stirring the reaction solution. More preferably, the heating in Step (A-2) is maintained. Specifically, the internal temperature of the reaction solution is more preferably in the range of 50 to 70° C., even more preferably approximately 60±5° C. The time over which the anhydrous oxalic acid solution is added dropwise is preferably approximately 1 to 2 hours, more preferably approximately 1 hour.

Step (A-4) is preferably performed under heating to prevent crystallization from proceeding after completion of the dropwise addition of the anhydrous oxalic acid solution to reduce the performance of stirring. The heating temperature is preferably in the range of 50 to 70° C., more preferably approximately 60±5° C., in terms of the internal temperature of the reaction solution as in Steps (A-2) and (A-3) described above. The stirring time is preferably 2 to 5 hours, more preferably 2 to 3 hours. In this context, (Step A) is the step of producing monohydrate crystals of a compound represented by formula (1b) and can thus achieve a favorable stirring efficiency and a shortened stirring time due to less contamination with an amorphous portion than that in conventional methods.

Step (A-5) is the step of cooling the reaction solution in order to complete crystallization and collect the crystals by filtration. The cooling temperature is preferably in the range of 20 to 40° C., more preferably approximately 30° C., in terms of the internal temperature of the reaction solution to maintain filtration performance. The filtration can be performed by usual natural filtration or filtration under reduced pressure.

Step (A-6) involves collecting the precipitated crystals by filtration, and washing the crystals, followed by drying. The solvent used in washing can be any of the solvents used above and is preferably acetonitrile. The amount of the solvent used in washing is preferably approximately 1 part by volume (V/W) with respect to 1 part of compound (1a). The crystals collected by filtration are dried and used in subsequent (Step B).

The monohydrate crystals of the compound represented by formula (1b) produced in the preceding (Step A) can be confirmed to include two types of crystal polymorphs. These two types of crystal polymorphs can be prepared, as described later in Examples, as: Form 2 monohydrate crystals that have characteristic peaks at diffraction angles (2θ) of 7.0 and 22.9° (±0.2°) in powder x-ray diffraction and exhibit the pattern shown in FIG. 4 in powder x-ray diffraction spectra; and Form 1 monohydrate crystals that have characteristic peaks at diffraction angles (2θ) of 8.5 and 26.5° (±0.2°) in powder x-ray diffraction and exhibit the pattern shown in FIG. 3 in powder x-ray diffraction spectra. The preferable aspect of the production method in (Step A) can selectively produce Form 2 monohydrate crystals of the compound represented by formula (1b), which serve as a more preferable starting material in next (Step B).

The second step (Step B) involves stirring the monohydrate crystals of the compound represented by formula (1b) in an organic solvent with a water content of less than 1% by weight under heating to produce anhydrous crystals of a compound represented by formula (1) based on crystal transformation.

In the present specification, "crystal transformation" refers to the change of a crystal structure to another across the barrier (threshold) of its stabilization energy by means of external energy, for example, heating. This event takes place in the presence of crystal polymorphs in compound crystals. Techniques or conditions for selectively preparing a polymorph by causing "crystal transformation" often differ depending on the compounds.

(B-1): A solvent is added to the monohydrate crystals of the compound represented by formula (1b) produced in the first step (Step A), and the reaction system is allowed to maintain the anhydrous state of the solvent and prevented from incorporating water therein to prepare a suspension or slurry in which the water content of the solvent is kept at less than 1% (1% by weight).

(B-2): The suspension or slurry is heated to an internal temperature of 60 to 80° C., and stirred after the solvent is confirmed to have a water content of less than 1% by weight.

(B-3): The solvent is distilled off under reduced pressure by heating to an internal temperature of 40° C. or higher and an external temperature of 80° C. or lower to azeotropically dehydrate water in the reaction solvent and thereby decrease the total volume of the solvent used by half or more in order to adjust the water content of the solvent in the reaction mixture to less than 0.2% by weight.

(B-4): A solvent is added thereto in the same amount as the amount distilled off, and the mixed solution is stirred at an internal temperature of 40 to 75° C. after the solvent in the reaction mixture is confirmed to have a water content of less than 0.2% by weight. In order to keep the water content at less than 0.2% by weight, the reaction system is allowed to maintain the anhydrous state of the added solvent and prevented from incorporating external humidity therein.

(B-5): The mixed solution is cooled to 20 to 40° C. with its water content kept at less than 0.2% by weight. This reaction may be carried out under an inert gas atmosphere with low humidity (water content) to prevent the reaction system from incorporating external humidity therein during the cooling.

(B-6): The precipitated crystals are collected, washed with the solvent used, and then dried.

Hereinafter, respective preferable aspects of Steps (B-1) to (B-6) will be described.

Step (B-1) involves adding a solvent to the monohydrate crystals represented by formula (1b) produced in the first step (Step A) to prepare a suspension or slurry. The solvent used can be a single or mixed organic solvent. Since the second step (Step B) is the step of producing anhydrous crystals, an anhydrous organic solvent is preferable. A commercially available anhydrous organic solvent may be used as the anhydrous organic solvent.

A single organic solvent or a mixed solvent of organic solvents can be used. Examples thereof can include one solvent or a mixed solvent of two or more selected from C1-C5 alkyl acetate solvents, linear or branched C1-C8 alcohol solvents, C1-C6 ketone solvents, toluene solvents, and C2-C5 nitrile solvents. Specific examples of these solvents are as defined above. These organic solvents may be used alone or as a mixture of two or more thereof. Since this step requires a low water content, a commercially available anhydrous organic solvent may be used. Among these organic solvents, acetonitrile, toluene, or a mixed solvent of acetonitrile and toluene is preferable, and acetonitrile is particularly preferable. The amount of the solvent used is preferably in the range of 5 to 30 parts by volume (V/W), more preferably 7 to 10 parts by volume (V/W), with respect to 1 part of compound (1b).

In this context, the solvent can be confirmed to have a water content of less than 1% (1% by weight) by a method known in the art for measuring the water content of a solvent, for example, the Karl Fischer method, and may be confirmed using a commercially available measurement apparatus such as a Karl Fischer moisture titrator.

Step (B-2) is the step of heating and stirring the suspension or slurry of (B-1). This step causes crystal transformation to proceed. The stirring temperature for crystal transformation is preferably in an internal temperature range of 60 to 80° C., more preferably 70 to 75° C. The stirring time needs to be 1 hour or longer and is preferably approximately 1 to 5 hours. In this context, the water content of the solvent in the mixed solution for or during stirring in Steps (B-1) and (B-2) is kept at less than 1% by weight to transform the monohydrate crystals of the compound represented by formula (1b) into the anhydrous crystals of the compound represented by formula (1). In order to keep the water content of the solvent at less than 1% by weight, the reaction system can be allowed to maintain the anhydrous state of the solvent and prevented from incorporating external humidity therein.

Step (B-3) involves distilling off the solvent by concentration. The temperature at which the solvent is distilled off by concentration is preferably an internal temperature of 40 to 75° C. and an external temperature of 80° C. or lower, more preferably an internal temperature of 45 to 60° C. and an external temperature of 80° C. or lower. The solvent can be distilled off by concentration under reduced pressure or normal pressure, preferably under reduced pressure. The solvent is preferably distilled off by concentration by half or more the total amount of the solvent. Specifically, this distilling off by concentration preferably decreases the amount of the solvent added in Step (B-1) by half or more. This distilling off procedure by concentration decreases the amount of water (water content) in the mixed solution system by azeotropic distillation with the organic solvent and prevents the anhydrous crystals from being rehydrated into monohydrate crystals. The water content of the solvent in the mixed solution is preferably less than 0.2% by weight, more preferably 0.15% by weight or less.

Step (B-4) involves adding a solvent in the same amount as the amount distilled off by concentration in Step (B-3) with the heating temperature of Step (B-3) kept, followed by stirring. The solvent added may be the same as or different from the solvent distilled off by concentration or may be a mixed solvent. The solvent added is preferably a single or mixed solvent of acetonitrile, methanol, and toluene, more preferably a single or mixed solvent of acetonitrile and toluene, particularly preferably a single solvent of acetonitrile. After the addition of the solvent, the suspension or slurry is preferably stirred at the same temperature as above for approximately 1 hour.

Step (B-5) involves cooling the mixed solution thus supplemented with the solvent and stirred in Step (B-4). The cooling can be performed by cooling the reactor from outside with water or the like or allowing it to cool spontaneously, resulting in an internal temperature in the range of 20 to 40° C. In the procedure in Step (B-4) and the cooling procedure in Step (B-5), the water content of the solvent in the mixed solution is kept at less than 0.2% by weight, more preferably 0.15% by weight or less. A preferable method adopted for keeping the water content at less than 0.2% by weight is, for example, to perform the reaction procedures under an inert gas atmosphere, as described above. The water content of the solvent thus kept at less than 0.2% by weight, more preferably 0.15% by weight or less, prevents the anhydrous crystals of the compound represented by formula (1) from being rehydrated and transformed into the monohydrate crystals of the compound represented by formula (1b). Thus, the stirring time in Step (B-5) is not particularly important, and the stirring can be performed for a time appropriate for the production schedule.

Step (B-6) involves collecting the precipitated crystals by filtration, and washing the crystals, followed by drying. The solvent used in washing can be the solvent used above and is preferably acetonitrile. The amount of the solvent used in washing is preferably approximately 1 part by volume (V/W) with respect to 1 part of compound (1b). The drying can be performed under normal pressure or reduced pressure, preferably at a temperature of approximately 40° C. In this context, the thus-dried anhydrous crystals of the compound represented by formula (1) of interest can be obtained at an overall yield of 60% or more based on compound (1b).

The anhydrous crystals of the compound represented by formula (1) produced in the preceding (Step B) can be confirmed to include two types of crystal polymorphs. These two types of crystal polymorphs can be prepared, as described later in Examples, as: Form 1 anhydrous crystals that have characteristic peaks at diffraction angles (2θ) of 5.1 and 20.4° (±0.2°) in powder x-ray diffraction and exhibit the pattern shown in FIG. 1 in powder x-ray diffraction spectra; and Form 2 anhydrous crystals that have characteristic peaks at diffraction angles (2θ) of 5.6 and 27.7° (±0.2°) in powder x-ray diffraction and exhibit the pattern shown in FIG. 2 in powder x-ray diffraction spectra. The preferable aspect of the production method in (Step B) can selectively produce Form 2 anhydrous crystals of the compound represented by formula (1), which are much less hygroscopic and more preferable, among the crystal polymorphs, as shown in Examples.

An alternative method of the second step (Step B) involves drying the monohydrate crystals of the compound represented by formula (1b) under reduced pressure under heating at 40° C. to obtain a compound represented by formula (1) as a dry solid that has substantially the same water content as in the anhydrous crystals of the compound represented by formula (1) and can be used in the subsequent production process. This alternative method, however, cannot be adopted as a process for producing actual pharmaceutical intermediates, due to an exceedingly long time required for the drying and low reproducibility on an industrial scale, though it can be carried out at a small-scale laboratory level. Alternatively, the second step (Step B) can involve treating the monohydrate crystals represented by formula (1b) with a base to form the free form (1a), which is then subjected to extraction procedures with an organic solvent such as toluene, followed by concentration procedures of the extracts to obtain the free form (1a) with a low water content. This approach, however, had an exceedingly low extraction efficiency of compound (1a) and significantly reduced operability and yields.

A feature of the present invention is to produce, with high purity at high yields compared with conventional methods, anhydrous crystals of a compound represented by formula (1) that is an important intermediate for the production of FXa inhibitor compound (X) or compound (X-a), by way of the step of producing monohydrate crystals of a highly pure compound represented by formula (1b) by utilizing the difference in water solubility between the cis-isomer and the trans-isomer (1-trans) of monohydrate crystals of the compound represented by formula (1b) and subsequently transforming the monohydrate crystals of the compound represented by formula (1b) into the anhydrous crystals of the compound represented by formula (1).

A feature of the present invention is the second step (Step B) involving producing anhydrous crystals of the compound represented by formula (1) by crystal transformation of the monohydrate crystals of the compound represented by formula (1b). Specific examples of a preferable aspect of the second step (Step B) can include the following operational scheme:

[Expression 1]

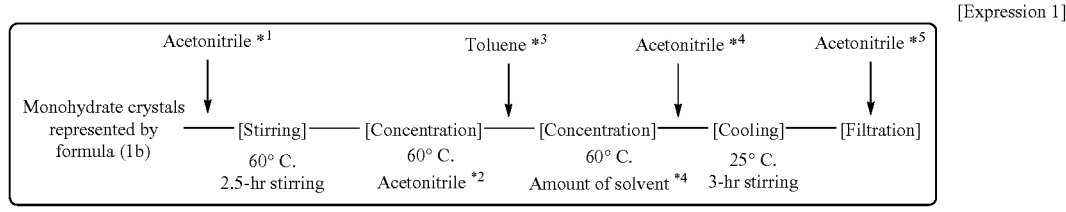

*1: 10 parts by volume (V/W) of acetonitrile with respect to 1 part of compound (1b) is added. The water content of the acetonitrile solvent is kept at 1% by weight or less. <Total amount of the solvent: 10 parts by volume with respect thereto>
*2: Half the amount (V) of acetonitrile added in *1 is distilled off by concentration to halve the amount (V). This concentration procedure can also distill off crystallization water eliminated by crystal transformation. Thus, the residual acetonitrile solvent has a water content less than 0.2% by weight. <Total amount of the solvent: 5 parts by volume>
*3: Toluene is added thereto in an amount corresponding to the amount distilled off by concentration in *2. <Total amount of the solvent: 10 parts by volume>
*4: The solvent is distilled off by concentration into 3/10 of the initial amount (10 parts by volume). After the concentration, high-boiling toluene remains in an amount 3/10 of the initial amount. <Total amount of the solvent: 3 parts by volume>
*5: Acetonitrile is added thereto in the same amount as the amount distilled off by concentration in *4. After the addition, the acetonitrile/toluene co-solvent has a water content less than 0.2% by weight. <Total amount of the solvent: 10 parts by volume>
*6: The crystals collected by filtration are washed with 1 part by volume (V/W) of acetonitrile with respect to 1 part of compound (1b).

This preferable aspect of (Step B) can selectively produce Form 2 anhydrous crystals of the compound represented by formula (1), one of the preferable crystal polymorphs.

Specific examples of a more preferable aspect of the second step (Step B), a feature of the present invention, can include the following operational scheme:

[Expression 2]

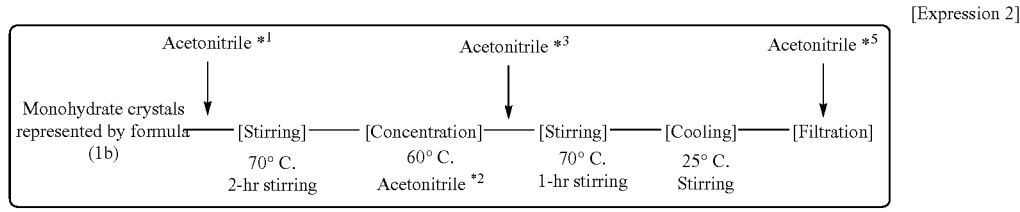

*1: 7 parts by volume (V/W) of acetonitrile with respect to 1 part of compound (1b) is added. The water content of the acetonitrile solvent is kept at 1% by weight or less. <Total amount of the solvent: 7 parts by volume with respect thereto>
*2: Acetonitrile added in *1 is distilled off by concentration by 4/7 of the volume (V). This concentration procedure can also distill off crystallization water eliminated by crystal transformation. Thus, the residual acetonitrile solvent has a water content less than 0.2% by weight. <Total amount of the solvent: 3/7 parts by volume>
*3: Acetonitrile is added thereto in the same amount as the amount distilled off by concentration in *2. After the addition, the residual acetonitrile solvent has a water content less than 0.2% by weight. <Total amount of the solvent: 7 parts by volume>
*4: The crystals collected by filtration are washed with 1 part by volume (V/W) of acetonitrile with respect to 1 part of compound (1b).

This more preferable aspect of (Step B) can selectively produce Form 2 anhydrous crystals of the compound represented by formula (1), one of the preferable crystal polymorphs.

The present invention provides a process for the preparation of anhydrous crystals of a compound represented by formula (1) by way of monohydrate crystals of a compound represented by formula (1b) from compound (2) and by crystal transformation thereof, as shown in the following scheme:

compound (2), and the amount of the metal azide salt used is preferably approximately 2.0 molar equivalents with respect to compound (2), though these amounts are not limited to these ranges in any way.

The amount of water used for preparing an azidification reagent complex from the quaternary ammonium salt and the metal azide salt is preferably approximately 1 to 2 parts by volume [1.0 (v/w)] with respect to 1 part by weight of the compound (2), though the amount is not limited to this range

[Formula 30]

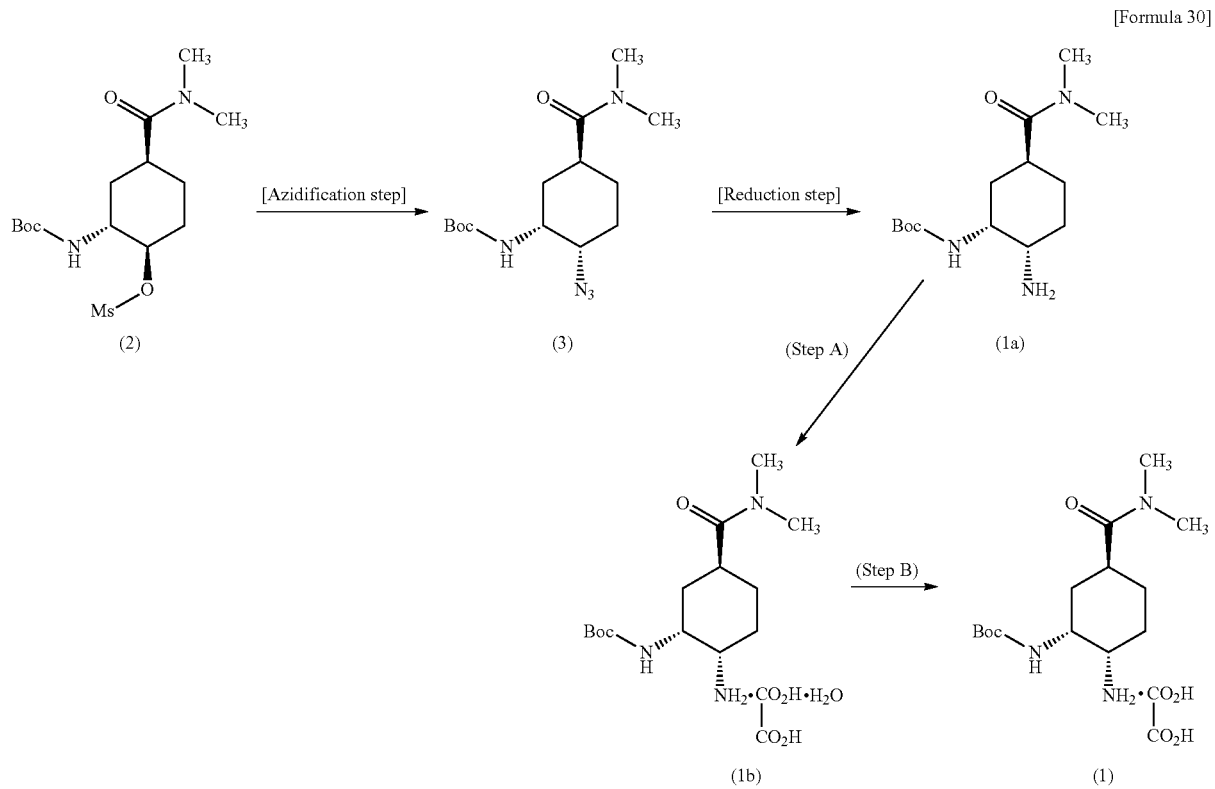

wherein Ms represents a methanesulfonyl group; and Boc represents a tert-butoxycarbonyl group.

[Azidification Step]:

Compound (2) is treated with an azidification reagent in a solvent to produce compound (3).

A quaternary ammonium salt and a metal azide salt are added to water to prepare an aqueous solution of an azidification reagent complex comprising quaternary ammonium salt-metal azide salt. Subsequently the aqueous solution is dehydrated using an aromatic hydrocarbon solvent to form a mixed solution of the azidification reagent complex comprising quaternary ammonium salt-metal azide salt and the aromatic hydrocarbon solvent with a water content of 0.2% by weight or less. Subsequently, compound (2) is treated with this mixed solution to produce compound (3).

The quaternary ammonium salt is preferably a quaternary ammonium salt of an alkylamine or a pyridinium salt, specifically particularly preferably ammonium chloride, 1-dodecylpyridinium chloride (also known as 1-laurylpyridinium chloride), or the like. The metal azide salt is preferably an alkali metal azide salt, more preferably sodium azide or lithium azide, particularly preferably sodium azide.

The amount of the quaternary ammonium salt used is preferably approximately 0.5 molar equivalents with respect to in any way. Water is preferably used in a small amount for its removal by the subsequent azeotropic dehydration procedure. The temperature for preparing the azidification reagent complex may be room temperature and is preferably in the range of 20 to 40° C. The dehydration means azeotropic dehydration using an organic solvent for azeotropy of water and is preferably azeotropic dehydration using an aromatic hydrocarbon solvent. The aromatic hydrocarbon solvent is preferably benzene, toluene, xylene, chlorobenzene, and dichlorobenzene. These solvents may be used alone (one thereof) or as a mixed solvent in which two or more thereof are mixed. The aromatic hydrocarbon solvent is more preferably toluene. The water content is preferably set to less than 0.2% by weight, more preferably 0.1% by weight or less, by azeotropic dehydration.

Preferably, compound (2) is subsequently added to the mixed solution of the azidification reagent complex and the aromatic hydrocarbon solvent, and the reaction mixture is treated at its internal temperature of 70° C. for approximately 18 hours with stirring.

After the completion of the reaction, the reaction mixture is preferably treated with an aqueous alkali solution as a work-up procedure. A solution of compound (3) in aromatic hydrocarbon is prepared by extraction with an aromatic hydrocarbon solvent. The aromatic hydrocarbon solvent is most preferably toluene. Specific examples of the production can include a method described in Reference Example 2.

[Reduction Step]:

This step involves reducing compound (3) to produce amino compound (1a). A method described in the pamphlet of International Publication No. WO 2007/032498 may be used. Compound (1a) can be obtained by the hydrogenolysis of compound (3) in the presence of a metal catalyst and a hydrogen source in a solvent. Various solvents can be used as the solvent. The solvent is preferably an alcohol solvent having 1 to 4 carbon atoms, such as methanol, ethanol, propanol, isopropanol (IPA), n-butanol, or t-butanol, particularly preferably methanol or ethanol. The reaction temperature is preferably room temperature to 70° C. The hydrogen source is preferably formic acid or formate, particularly preferably ammonium formate. The ammonium formate can be used in the range of approximately 5 to 10 parts by mol with respect to 1 part by mol of compound (3). The metal catalyst can be any metal catalyst usually used in this kind of hydrogenolysis, and examples thereof can include palladium-carbon, Raney nickel, and Raney cobalt. Palladium-carbon is preferable.

(Step A) and (Step B):

These steps are performed in the same way as (Step A) and (Step B) described above.

A specific aspect of the feature of the present invention, i.e., the production of anhydrous crystals of a compound represented by formula (1) by way of monohydrate crystals of a compound represented by formula (1b) from compound (2) and by crystal transformation thereof will be described later in Examples.

Compound (2) (methanesulfonyloxy derivative) described above can be produced, for example, as shown in [Scheme 1] below. Specific examples of the production can include a method described in Reference Example 1.

Specifically, compound (2) can be produced by producing compound (11) from compound (10) and methanesulfonylating this compound (11). Compounds (10) and (11) can be produced by methods described in the pamphlet of International Publication No. WO 2007/032498.

[Formula 31]

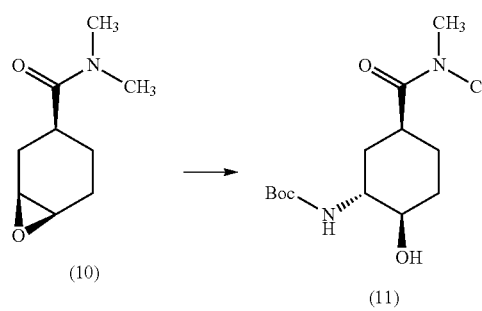

(10)    (11)

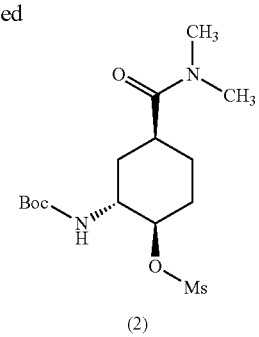

(2)

wherein Ms represents a methanesulfonyl group; and Boc represents a tert-butoxycarbonyl group.

The highly pure anhydrous crystals represented by formula (1) produced in the present invention can be used to produce FXa inhibitor compound (X) or compound (X-a) as shown below. Use of the anhydrous crystals of the highly pure compound represented by formula (1) allows the production of highly pure compound (X) or compound (X-a).

Compound (5) (amide derivative) can be produced from the anhydrous crystals of the highly pure compound represented by formula (1) of the present invention in the presence of tertiary amine, as shown in the following scheme:

[Formula 32]

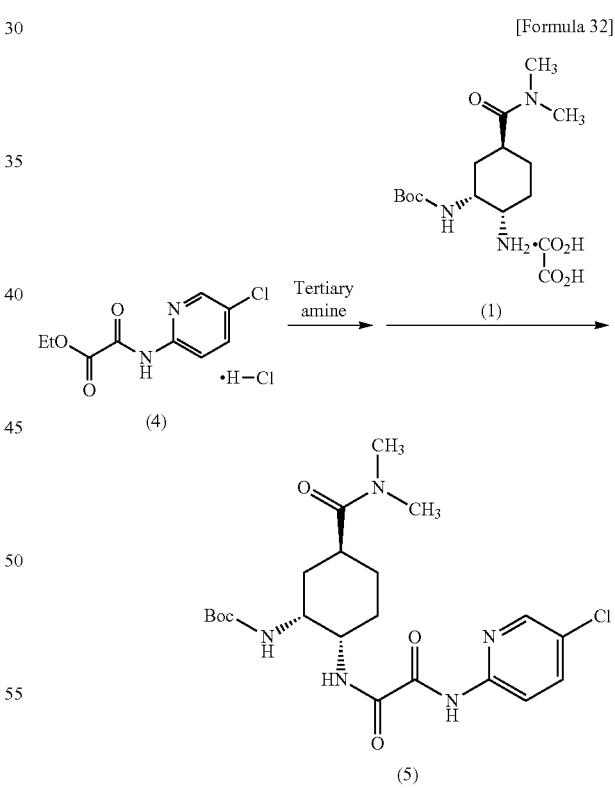

wherein Boc represents a tert-butoxycarbonyl group.

Compound (4) can be produced as shown below. Specific examples of the production can include the method described in Reference Example 4. Specifically, compound (4) can be produced by adding a commercially available aniline derivative as compound (4b) to compound (4c) in a C2-C4 nitrile solvent with stirring.

[Formula 33]

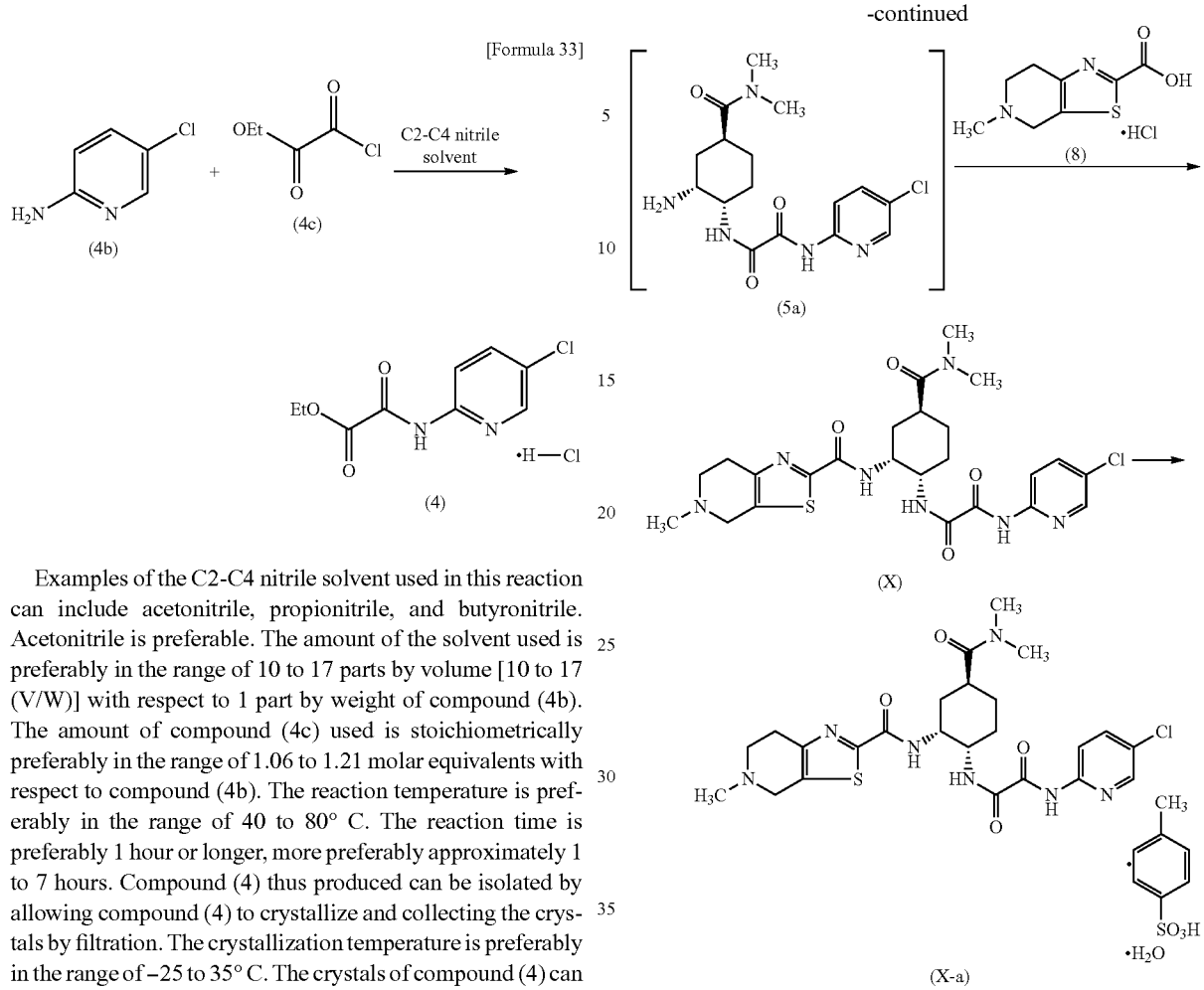

Examples of the C2-C4 nitrile solvent used in this reaction can include acetonitrile, propionitrile, and butyronitrile. Acetonitrile is preferable. The amount of the solvent used is preferably in the range of 10 to 17 parts by volume [10 to 17 (V/W)] with respect to 1 part by weight of compound (4b). The amount of compound (4c) used is stoichiometrically preferably in the range of 1.06 to 1.21 molar equivalents with respect to compound (4b). The reaction temperature is preferably in the range of 40 to 80° C. The reaction time is preferably 1 hour or longer, more preferably approximately 1 to 7 hours. Compound (4) thus produced can be isolated by allowing compound (4) to crystallize and collecting the crystals by filtration. The crystallization temperature is preferably in the range of −25 to 35° C. The crystals of compound (4) can be isolated by collection by filtration. Compound (4) collected by filtration may be used in a dry state (dry form) after drying under normal pressure or reduced pressure or may be used in a wet state (wet form).

Highly pure FXa inhibitor compound (X) and the compound represented by formula (X-a) (mono-p-toluenesulfonate monohydrate of compound (X)) can be produced by a method disclosed in Patent Literature 1 or 3 using compound (5) produced from the anhydrous crystals of the compound represented by formula (1) of the present invention. Specifically, these compounds can be produced as shown in the following scheme and Reference Examples 6 and 7 described later:

[Formula 34]

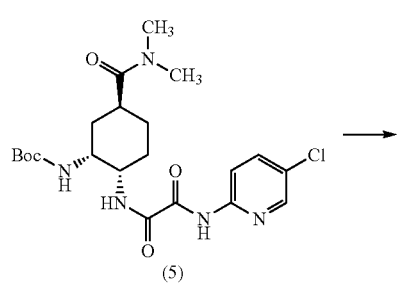

wherein Boc represents a tert-butoxycarbonyl group.

The anhydrous crystals of the highly pure compound (1), a feature of the present invention, can be used to produce highly pure FXa inhibitor compound (X) and compound (X-a) (mono-p-toluenesulfonate monohydrate of compound (X)).

The purity of compound (X-a) produced by the preparation process of the present invention was quantitatively measured according to a routine method using usual HPLC on the basis of the peak areas of the related compounds derived from the production process, impurities, etc. A commercially available normal-phase column, reverse-phase column, or chiral column thereof was used for quantitative analysis in HPLC. A solvent system whose retention time (Rt) did not overlap with that of the related compounds or impurities was selected for use as the mobile phase. Also, respective pure standards of the related compounds and impurities were produced, and calibration curves were prepared for the quantification of these related compounds and impurities. The purity of compound (X-a) produced by the production method of the present invention was analyzed on the basis of the calibration curves. As a result, bulk compound (X-a) produced by the production method of the present invention was free from related compounds or impurities each individually exceeding 0.1% by weight. The total amount of the related compounds and impurities was approximately 0.17 to 0.19% by weight in two measured lots, though somewhat differing depending on production lots.

The purity of compound (X-a) produced by the production method of the present invention is preferably 98.5% by weight or more, 99.0% by weight or more, 99.30% by weight or more, 99.50% by weight or more, 99.60% by weight or more, 99.70% by weight or more, 99.75% by weight or more, 99.80% by weight or more, 99.85% by weight or more, 99.90% by weight or more, 99.95% by weight or more, or 99.99% by weight or more.

EXAMPLES

Next, the present invention will be described in detail with reference to the Examples. However, the present invention is not intended to be limited to these in any way.

Tetramethylsilane was used as the internal standard for the nuclear magnetic resonance (NMR) spectra. Abbreviations showing multiplicity represent s=singlet, d=doublet, t=triplet, q=quartet, m=multiplet, and brs=broad singlet.

Reference Example 1

(1R,2R,4S)-2-[(tert-Butoxycarbonyl)amino]-4-[(dimethylamino)carbonyl]cyclohexylmethanesulfonate (2)

[Formula 35]

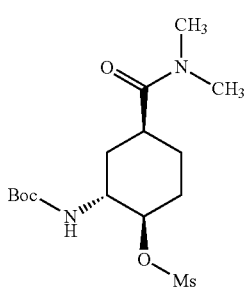

(2)

wherein Boc represents a tert-butoxycarbonyl group; and Ms represents a methanesulfonyl group.

[Step 1] Synthesis of tert-butyl {(1R,2R,5S)-5-[(dimethylamino)carbonyl]-2-hydroxycyclohexylcarbonyl}carbamate (11)

[Formula 36]

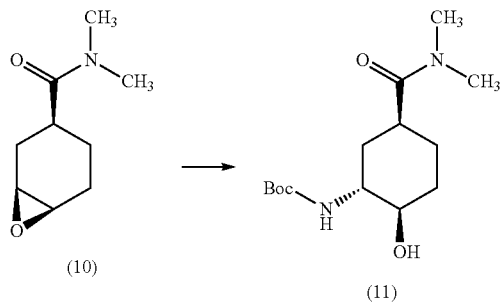

wherein Boc is as defined above.

A 28% aqueous ammonia solution (5 ml) was added to (1S,3S,6R)—N,N-dimethyl-7-oxabicyclo[4.1.0]heptane-3-carboxamide (10) (1 g) at room temperature. The mixed solution was stirred at 40° C. for hours, and then, the solvent was concentrated under reduced pressure to obtain (1S,3R,4R)-3-amino-4-hydroxy-N,N-dimethylcyclohexanecarboxamide (1.18 g).

The obtained (1S,3R,4R)-3-amino-4-hydroxy-N,N-dimethylcyclohexanecarboxamide (1.18 g) was dissolved in water (5 ml). To the solution, di-tert-butyl dicarbonate (1.93 g) and a 10 N aqueous sodium hydroxide solution (1.5 ml) were then added at room temperature. The reaction mixture was stirred at 40° C. for 2 hours and then subjected to extraction with 4-methyl-2-pentanone (MIBK) (5 ml) three times, and the solvent in the extracts was distilled off under reduced pressure. To the residue, 4-methyl-2-pentanone (MIBK) (3 ml) was added, and the mixture was stirred at room temperature. The precipitated crystals were collected by filtration and dried to obtain the title compound (11) (1.26 g).

$^1$H-NMR (CDCl$_3$) δ: 1.44 (9H, s), 1.48-1.59 (2H, m), 1.77-1.78 (2H, m), 1.86-1.97 (1H, m), 2.11-2.17 (1H, m), 2.78-2.83 (1H, m), 2.92 (3H, s), 3.02 (3H, s), 3.53-3.60 (1H, m), 3.94 (1H, br. s), 4.52-4.68 (1H, m).

[Step 2] Synthesis of (1R,2R,4S)-2-[(tert-butoxycarbonyl)amino]-4-[(dimethylamino)carbonyl]cyclohexylmethanesulfonate (2)

[Formula 37]

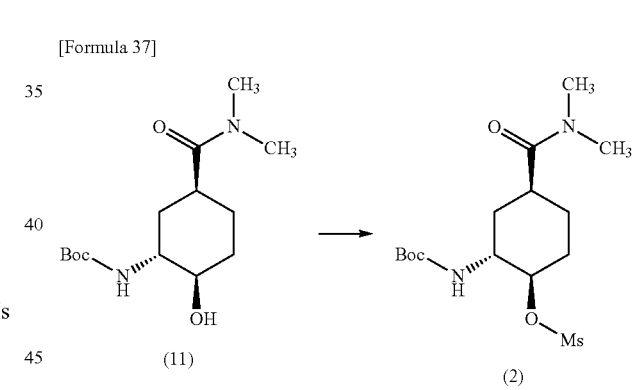

wherein Boc and Ms are as defined above.

Methanesulfonyl chloride (159.07 g) was added to a solution of tert-butyl {(1R,2R,5S)-5-[(dimethylamino)carbonyl]-2-hydroxycyclohexylcarbonyl}carbamate (11) (214.59 g) in 4-methyl-2-pentanone (MIBK) (1875 ml) with stirring at room temperature. To the mixed solution, triethylamine (170.62 g) was added at room temperature, and the mixture was stirred at this temperature for 1 hour. To the reaction solution, water was added, and then, the organic layer was separated. The solvent was concentrated under reduced pressure. To the concentrated residue, MIBK (750 ml) was then added, and the mixture was stirred at room temperature for 3 hours. The precipitated crystals were collected by filtration and dried to obtain the title compound (2) (242.57 g).

$^1$H-NMR (CDCl$_3$) δ: 1.45 (9H, s), 1.58-1.66 (1H, m), 1.67-1.76 (1H, m), 1.84-1.96 (2H, m), 2.04-2.15 (1H, m), 2.17-2.26 (1H, m), 2.75-2.81 (1H, m), 2.94 (3H, s), 3.04 (3H, s), 3.07 (3H, s), 4.00-4.08 (1H, m), 4.69-4.82 (2H, m).

Reference Example 2 tert-Butyl {(1R,2R,5S)-2-azido-5-[(dimethylamino)carbonyl]cyclohexyl}carbamate (3) (Production Method Described in the Pamphlet of International Publication No. WO 2007/032498)

[Formula 38]

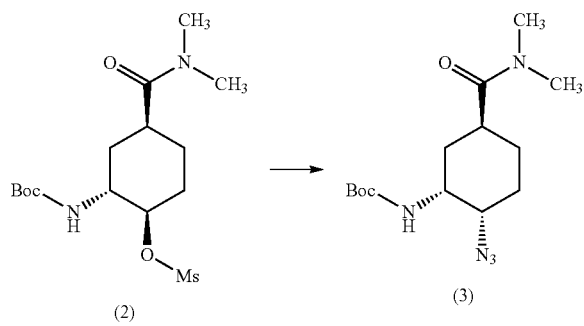

wherein Ms represents a methanesulfonyl group; and Boc represents a tert-butoxycarbonyl group.

Sodium azide (7.14 g) and dodecylpyridinium chloride (7.80 g) were added to a solution of (1R,2R,4S)-2-[(tert-butoxycarbonyl)amino]-4-[(dimethylamino)carbonyl]cyclohexylmethanesulfonate (2) (20.0 g) in N,N-dimethylacetamide (DMAC) (40 ml) at room temperature. The mixed solution was stirred at 60° C. for 72 hours and then allowed to cool to room temperature. To the reaction solution, water was added, followed by extraction with ethyl acetate. The extracts were washed with a saturated aqueous solution of sodium bicarbonate and water, and then, the solvent was concentrated under reduced pressure. To the concentrated residue, an n-hexane-ethyl acetate (5:1) mixed solvent (300 ml) was added, and the mixture was stirred at room temperature for 1 hour. The precipitated crystals were collected by filtration. The procedure of adding an n-hexane-ethyl acetate (5:1) mixed solvent (300 ml) to the obtained crystals, followed by stirring and crystal collection by filtration was repeated twice to obtain the title compound (3) (4.6 g, 26.9%).
$^1$H-NMR (CDCl$_3$) δ: 1.46 (9H, s), 1.55-1.74 (3H, m), 1.75-1.82 (1H, m), 2.02-2.12 (2H, m), 2.74-2.83 (1H, m), 2.93 (3H, s), 3.02 (3H, s), 3.72-3.78 (1H, m), 4.07-4.13 (1H, m), 4.61-4.66 (1H, m).

Reference Example 3 tert-Butyl {(1R,2S,5S)-2-amino-5-[(dimethylamino)carbonyl]cyclohexyl}carbamate oxalate (1) (Production Method Described in the Pamphlet of International Publication No. WO 2007/032498)

[Formula 39]

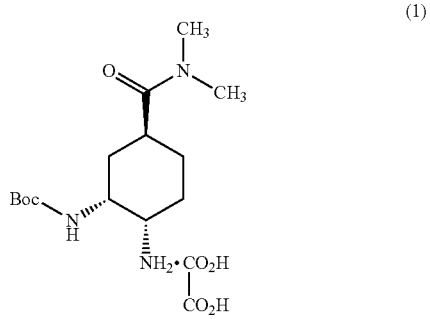

wherein Boc represents a tert-butoxycarbonyl group.

Sodium azide (7.14 g) and dodecylpyridinium chloride (7.80 g) were added to a solution of (1R,2R,4S)-2-[(tert-butoxycarbonyl)amino]-4-[(dimethylamino)carbonyl]cyclohexylmethanesulfonate (2) (20.0 g) in toluene (100 ml) at room temperature. The mixed solution was stirred at 60° C. for 72 hours and then allowed to cool to room temperature. To the reaction solution, water was added, and the organic layer was separated. The organic layer was washed with a saturated aqueous solution of sodium bicarbonate and water, and then, the solvent was distilled off.

To the residue, methanol, and then 7.5% Pd—C and ammonium formate were added, and the mixture was stirred at 40° C. for 1 hour. Pd—C was filtered off, and then, the solvent was concentrated under reduced pressure. To this residue, aqueous acetonitrile (200 ml) and anhydrous oxalic acid (4.94 g) were added, and the mixture was stirred at room temperature for 17 hours. The precipitated crystals were collected by filtration. The obtained crystals were added to acetonitrile (200 ml), and the mixture was stirred at 40° C. for 24 hours. The precipitated crystals were collected by filtration and dried to obtain the title compound (1) (12.7 g).
$^1$H-NMR (D$_2$O) δ: 1.30 (9H, s), 1.37-1.49 (2H, m), 1.63 (1H, t, J=2.7 Hz), 1.72-1.83 (3H, m), 2.77 (3H, s) 2.80 (1H, t, J=12.4 Hz), 2.96 (3H, m), 3.32 (1H, d, J=12.2 Hz), 4.10 (1H, br).

Anal.: C$_{16}$H$_{29}$N$_3$O$_7$.

Theoretical: C, 50.70%, H, 7.75%, N, 10.96%.

Found: C, 51.19%, H, 7.79%, N, 11.19%.

Reference Example 4

Ethyl 2-[(5-chloropyridin-2-yl)amino]-2-oxoacetate monohydrochloride (4) (Production Method Described in the Pamphlet of International Publication No. WO 2007/032498)

[Formula 40]

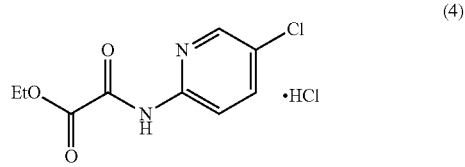

Ethyl oxalyl chloride (11.7 g) was added to a suspension of 2-amino-5-chloropyridine (10.0 g) in acetonitrile (120 ml) at 50° C., and the mixture was stirred at this temperature for 2 hours. The reaction solution was cooled, and crystals were collected by filtration at 10° C., washed with acetonitrile (40 ml), and then dried under reduced pressure to obtain the title compound (4) (19.7 g).

Reference Example 5 tert-Butyl (1R,2S,5S)-2-({2-[(5-chloro-2-pyridin-2-yl)amino]-2-oxoacetyl}amino)-5-(dimethylaminocarbonyl)cyclohexylcarbamate (5) (Production Method Described in the Pamphlet of International Publication No. WO 2007/032498)

Reference Example 6

$N^1$-(5-Chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide (X) (Production Method Described in the Pamphlet of International Publication No. WO 2007/032498)

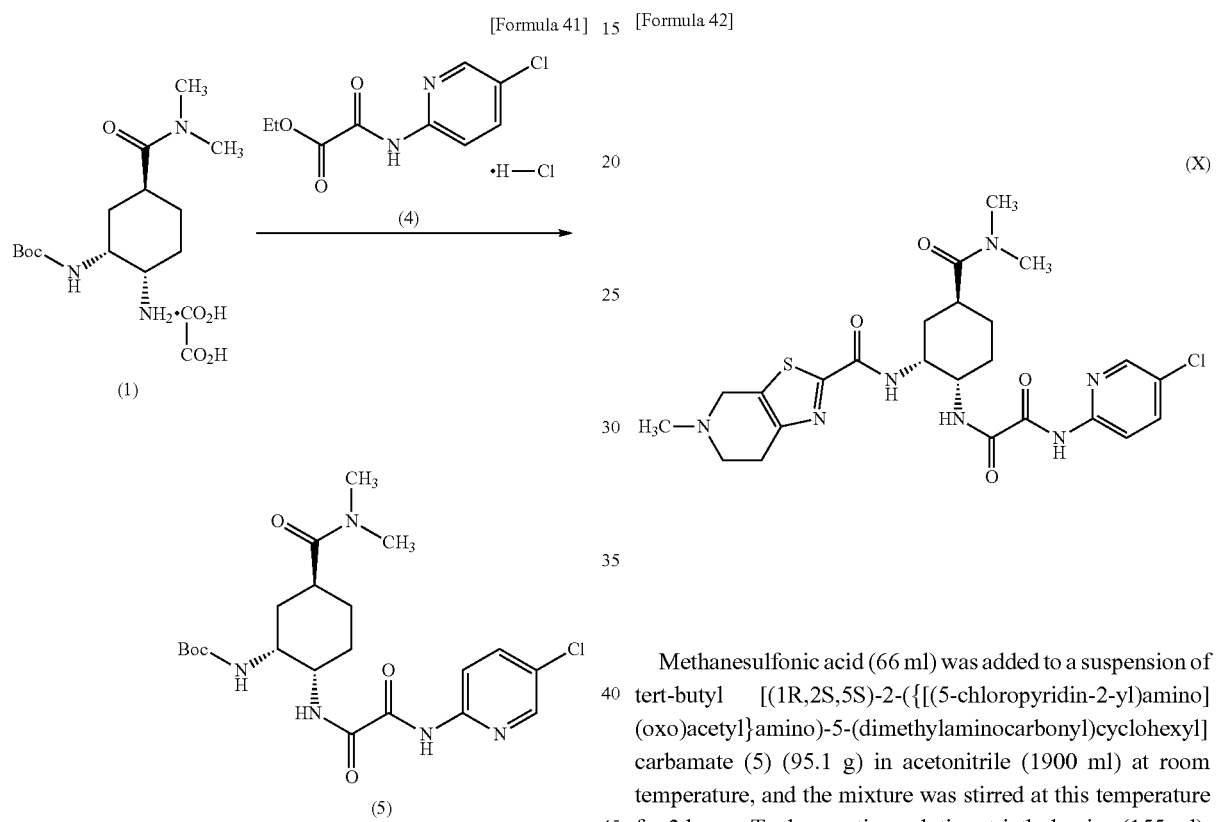

wherein Boc represents a tert-butoxycarbonyl group.

Triethylamine (169 ml) was added to a suspension of tert-butyl (1R,2S,5S)-2-amino-5-(dimethylaminocarbonyl)cyclohexylcarbamate monooxalate (1) (100.1 g) in acetonitrile (550 ml) at 60° C. Ethyl 2-[(5-chloropyridin-2-yl)amino]-2-oxoacetate monohydrochloride (4) (84.2 g) was added thereto at this temperature, and the mixture was stirred for 6 hours and then stirred at room temperature for 16 hours. To the reaction solution, water was added, and the mixture was stirred at 10° C. for 1.5 hours. Then, crystals were collected by filtration to obtain the title compound (5) (106.6 g).

$^1$H-NMR (CDCl$_3$) δ: 1.25-1.55 (2H, m), 1.45 (9H, s), 1.60-2.15 (5H, m), 2.56-2.74 (1H, br. s), 2.95 (3H, s), 3.06 (3H, s), 3.90-4.01 (1H, m), 4.18-4.27 (1H, m), 4.70-4.85 (0.7H, br), 5.70-6.00 (0.3H, br. s), 7.70 (1H, dd, J=8.8, 2.4 Hz), 7.75-8.00 (1H, br), 8.16 (1H, br.d, J=8.8 Hz), 8.30 (1H, d, J=2.4 Hz), 9.73 (1H, s).

Methanesulfonic acid (66 ml) was added to a suspension of tert-butyl [(1R,2S,5S)-2-({[(5-chloropyridin-2-yl)amino](oxo)acetyl}amino)-5-(dimethylaminocarbonyl)cyclohexyl]carbamate (5) (95.1 g) in acetonitrile (1900 ml) at room temperature, and the mixture was stirred at this temperature for 2 hours. To the reaction solution, triethylamine (155 ml), 5-methyl-4,5,6,7-tetrahydro[1,3]thiazolo[5,4-c]pyridine-2-carboxylic acid hydrochloride (8) (52.5 g), 1-hydroxybenzotriazole (33.0 g), and 1-ethyl-3-(3-dimethylaminopropyl)carbodiimide hydrochloride (46.8 g) were added under ice cooling, and the mixture was stirred at room temperature for 16 hours. Triethylamine and water were added thereto, and the mixture was stirred for 1 hour under ice cooling. Then, crystals were collected by filtration to obtain the title compound (X) (103.2 g).

$^1$H-NMR (CDCl$_3$) δ: 1.60-1.98 (3H, m), 2.00-2.16 (3H, m), 2.52 (3H, s), 2.78-2.90 (3H, m), 2.92-2.98 (2H, m), 2.95 (3H, s), 3.06 (3H, s), 3.69 (1H, d, J=15.4 Hz), 3.75 (1H, d, J=15.4 Hz), 4.07-4.15 (1H, m), 4.66-4.72 (1H, m), 7.40 (1H, dd, J=8.8, 0.6 Hz), 7.68 (1H, dd, J=8.8, 2.4 Hz), 8.03 (1H, d, J=7.8 Hz), 8.16 (1H, dd, J=8.8, 0.6 Hz), 8.30 (1H, dd, J=2.4, 0.6 Hz), 9.72 (1H, s).

MS (ESI) m/z: 548 (M+H)$^+$.

Reference Example 7

N¹-(5-Chloropyridin-2-yl)-N²-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide mono-p-toluenesulfonate monohydrate (X-a) (Production Method Described in the Pamphlet of International Publication No. WO 2007/032498)

[Formula 43]

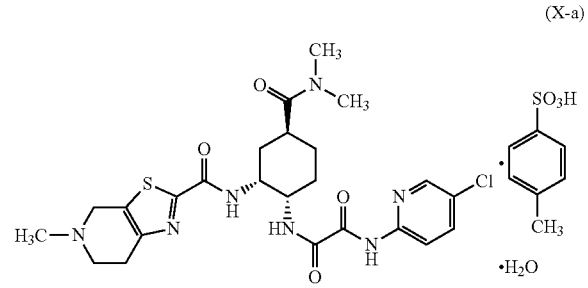

(X-a)

N¹-(5-Chloropyridin-2-yl)-N²-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide (X) (6.2 g) was dissolved in methylene chloride (120 ml). To the solution, a 1 mol/L solution of p-toluenesulfonic acid in ethanol (11.28 ml) was added, and the solvent was distilled off. To the residue, 15% hydrous ethanol (95 ml) was added, and the mixture was dissolved by stirring at 60° C. Then, the mixture was cooled to room temperature and stirred for 1 day. The precipitated crystals were collected by filtration, washed with ethanol, and then dried under reduced pressure at room temperature for 2 hours to obtain the title compound (X-a) (7.4 g).

$^1$H-NMR (DMSO-$d_6$) δ: 1.45-1.54 (1H, m), 1.66-1.78 (3H, m), 2.03-2.10 (2H, m), 2.28 (3H, s), 2.79 (3H, s), 2.91-3.02 (1H, m), 2.93 (3H, s), 2.99 (3H, s), 3.13-3.24 (2H, m), 3.46-3.82 (2H, m), 3.98-4.04 (1H, m), 4.43-4.80 (3H, m), 7.11 (2H, d, J=7.8 Hz), 7.46 (2H, d, J=8.2 Hz), 8.01 (2H, d, J=1.8 Hz), 8.46 (1H, t, J=1.8 Hz), 8.75 (1H, d, J=6.9 Hz), 9.10-9.28 (1H, br), 10.18 (1H, br), 10.29 (1H, s).

MS (ESI) m/z: 548 (M+H)⁺.

Anal.: $C_{24}H_{30}ClN_7O_4S \cdot C_7H_8O_3S \cdot H_2O$

Theoretical: C, 50.43; H, 5.46, N, 13.28, Cl; 4.80, S; 8.69.
Found: C, 50.25; H, 5.36, N, 13.32, Cl; 4.93, S; 8.79.
mp (dec.): 245-248° C.

Reference Example 8

A compound represented by formula (1) was produced from compound (1a) and anhydrous oxalic acid according to the description of the pamphlet of International Publication No. WO 2007/032498, and the rate of contamination of compound (1) with its trans-isomer compound (1-trans) was determined. Compound (1a) includes approximately 10% of its trans-isomer compound (1a-trans) at a ratio similar to the formation ratio between the cis-isomer and the trans-isomer derived from azidification described in Reference Example 157 of the pamphlet of International Publication No. WO 2001/74774, though these production methods differ in substrate.

TABLE 1

| | Rate of contamination with trans-compound (1-trans) | | |
|---|---|---|---|
| | Percentage of (1a-trans) immediately after (1a) production | Percentage of (1-trans) in compound (1) after (first crystallization) | Percentage of (1-trans) in compound (1) after (second crystallization) |
| Run 1 | 9.7% | 3.4% | 1.01% |
| Run 2 | 10.2% | 4.2% - | 7.69% |
| Run 3 | — | 3.7%-6.7% Increased in proportion to stirring time | 8.61% |

<Results>

The production of compound (1) by way of two crystallization steps described in the pamphlet of International Publication No. WO 2007/032498 was examined for the rate of time-dependent contamination with its related compound (1-trans) in the first crystallization. As a result, the rate of contamination was approximately 1 to 3% for Run 1, whereas it was 4.2% or more and 3.7 to 6.7% (increased in proportion to the stirring time) for Run 2 and Run 3, respectively. As is evident from these results, the rate of contamination with the related compound (1-trans) was drastically increased with an increase in stirring time and was approximately 1.5 to 2.5 times larger than the percentage content described in the pamphlet of International Publication No. WO 2007/032498.

Reference Example 9

Compound (1) was produced from compound (1a) and anhydrous oxalic acid according to the description of the pamphlet of International Publication No. WO 2007/032498, and the rate of contamination of compound (1) with its trans-isomer compound (1-trans) depending on the stirring time was determined. The results are shown in Table 2.

TABLE 2

| Stirring time | Conventional method | Amount of crystallization solvent increased by 1.18 times | Amount of crystallization solvent increased by 1.3 times |
|---|---|---|---|
| 0 hr | 3.65% | 3.89% | 3.56% |
| 15 hr | 3.63% | — | — |
| 24 hr | 8.65% | 3.93% | 3.58% |
| 57 hr | | 8.74% | 3.62% |
| 7 days | | | 3.66% |
| 9 days | | | 5.60% |

<Results>

For the purpose of reducing the rate of contamination with the related compound (1-trans) shown in Table 1 above, the amount of the crystallization solvent in the (second crystallization) was increased and examined for its effect. The examination results shown in Table 2 demonstrated that a longer stirring time drastically increased the rate of contamination with the related compound (1-trans) even when the amount of the solvent was increased. These results raised concerns about the robustness of the production method based on crystallization.

As shown in Tables 1 and 2, the production of compound (1) by way of two crystallization steps according to the conventional method (production method described in the pamphlet of International Publication No. WO 2007/032498) was examined for time-dependent change in the rate of contamination with its related compound (1-trans) in the first crystallization. These results revealed that a longer stirring time drastically increased the rate of contamination with the related compound (1-trans) and increased this rate by approximately 1.5 to 2.5 times. Also, increase in the amount of the solvent used proportionally reduced the rate of contamination with the related compound (1-trans), whereas a longer stirring time drastically increased the rate of contamination therewith. These results raised concerns about the robustness of this production process from the viewpoint of quality control against impurities or the like in industrial production.

Reference Example 10

Time-dependent change in the crystal form of precipitated crystals in the first crystallization according to the conventional method (the pamphlet of International Publication No. WO 2007/032498) from compound (1a) and anhydrous oxalic acid was determined by powder x-ray diffraction.
<Results>

The powder x-ray crystal diffraction diagram showed that the crystals from the first crystallization in the conventional method (International Publication No. WO 2007/032498) were amorphous immediately after their precipitation. Also, immediately after the precipitation of these crystals in the first crystallization, an amorphous portion attributed to local supersaturation was visually observed at areas that had undergone the dropwise addition of the oxalic acid solution. As is evident from these results, the crystal form varied depending on the rate of dropwise addition of the oxalic acid solution (the time over which the oxalic acid solution was added dropwise), and this method presented problems associated with the stability of the crystallization step and as such, was shown to be unsuitable as an industrial production method.

Example 1

Crystal Polymorphs (Form 1 Anhydrous Crystals and Form 2 Anhydrous Crystals) of Anhydrous Crystals of tert-butyl {(1R,2S,5S)-2-amino-5-[(dimethylamino)carbonyl]cyclohexyl}carbamate oxalate (1)

[Formula 44]

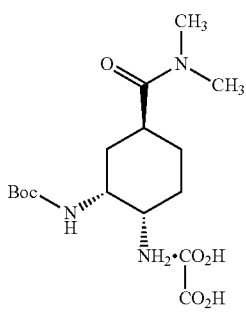

(1)

wherein Boc represents a tert-butoxycarbonyl group.

Figure 2:
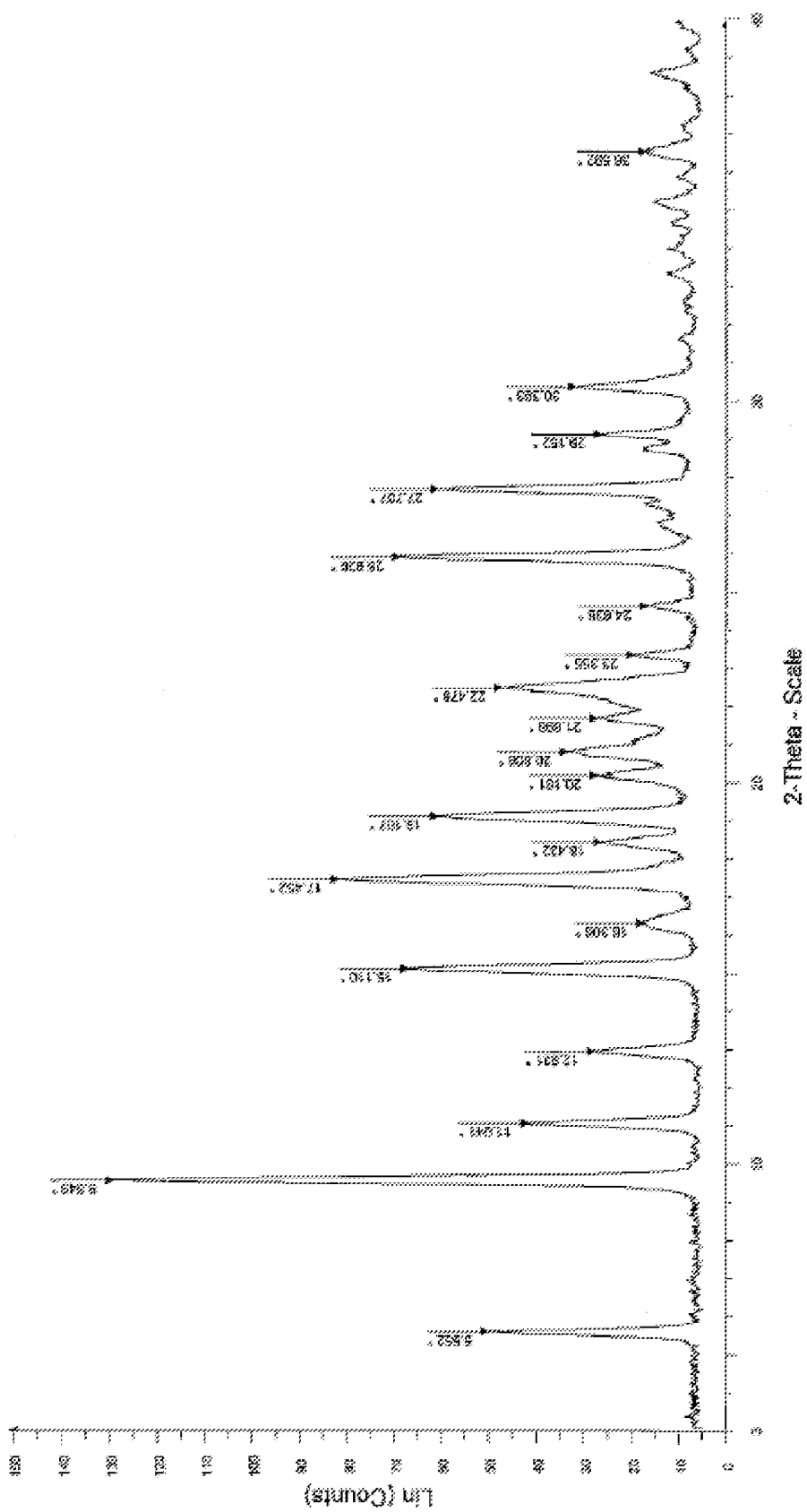
FIG. 2 shows a powder x-ray diffraction diagram of Form 2 anhydrous crystals of the compound represented by formula (1).
Figure 5:
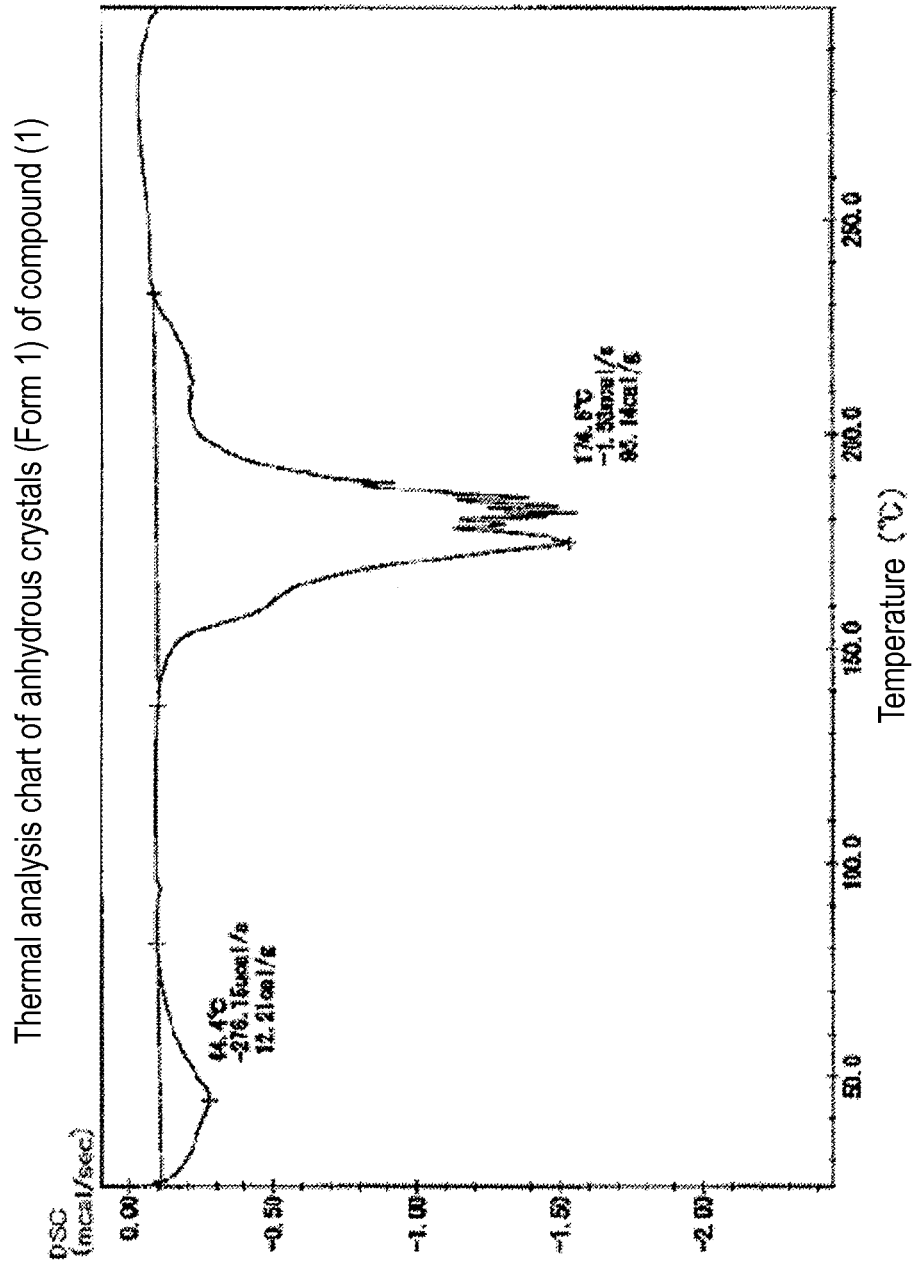
FIG. 5 shows a thermal analysis chart of anhydrous crystals (Form 1) of the compound represented by formula (1).
Figure 6:
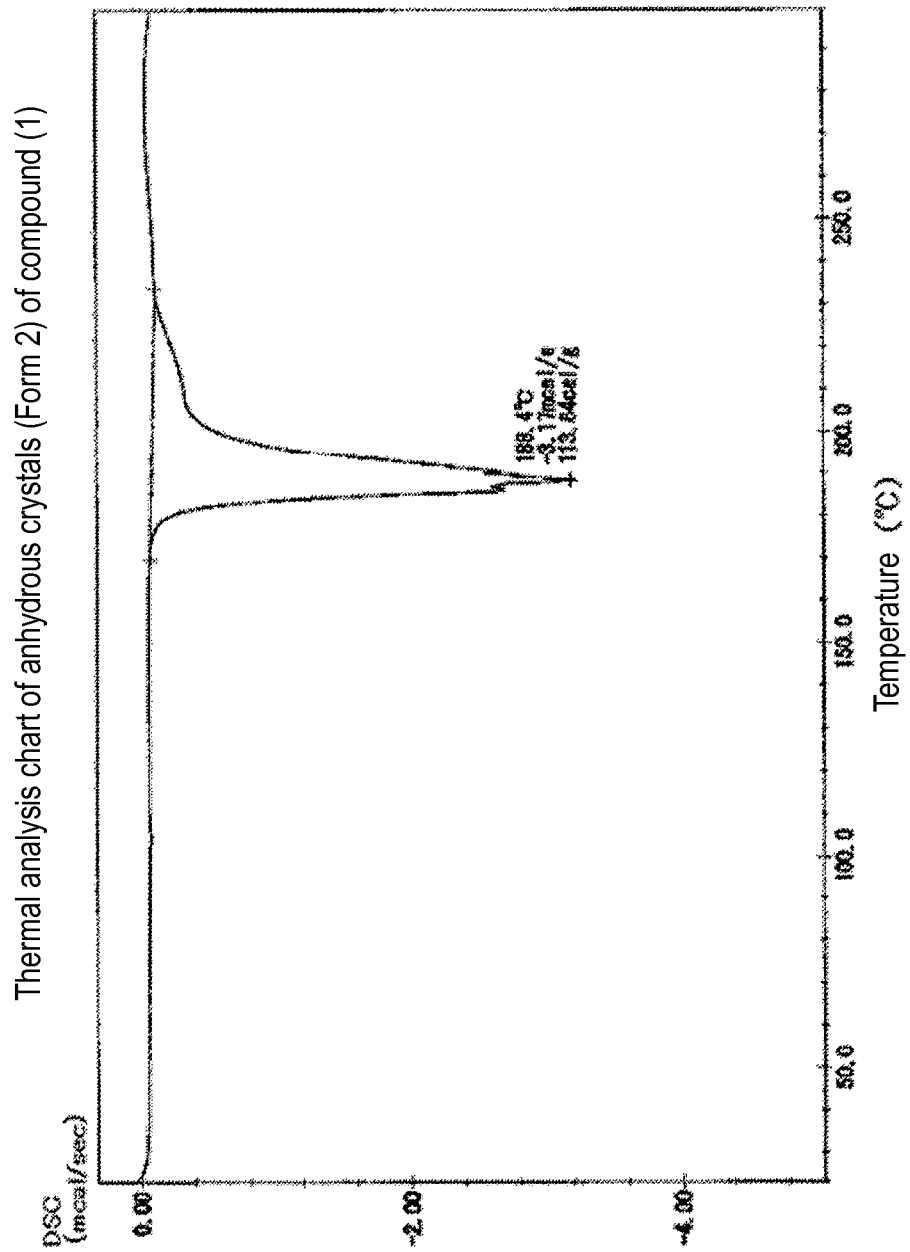
FIG. 6 shows a thermal analysis chart of anhydrous crystals (Form 2) of the compound represented by formula (1).

Anhydrous crystals of compound (1) produced by the method described in Reference Example 3 were found to be transformed to monohydrate crystals by stirring at 25° C., depending on the percentage water content of the mother liquor. Unlike the production method of Reference Example 3, a method involving keeping the percentage water content of the acetonitrile solution at 0.65% or less and treating the reaction solution at a stirring temperature of 60 to 80° C. for 1 hour or longer produced Form 2 anhydrous crystals, which were hardly transformed to monohydrate crystals, rather than the preceding Form 1 anhydrous crystals. The Form 2 anhydrous crystals were also found to be excellent in operability such as filtration performance. Powder x-ray diffraction diagrams of the Form 1 and Form 2 anhydrous crystals of compound (1) are shown in FIGS. 1 and 2, respectively, and their diffraction diagrams based on thermal analysis are shown in FIGS. 5 and 6, respectively.

Example 2

Crystal Polymorphs (Form 1 Monohydrate Crystals and Form 2 Monohydrate Crystals) of tert-butyl {(1R,2S,5S)-2-amino-5-[(dimethylamino)carbonyl]cyclohexyl}carbamate oxalate monohydrate (1b)

[Formula 45]

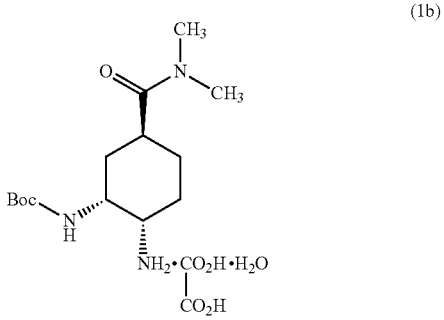

(1b)

wherein Boc represents a tert-butoxycarbonyl group.

Figure 3:
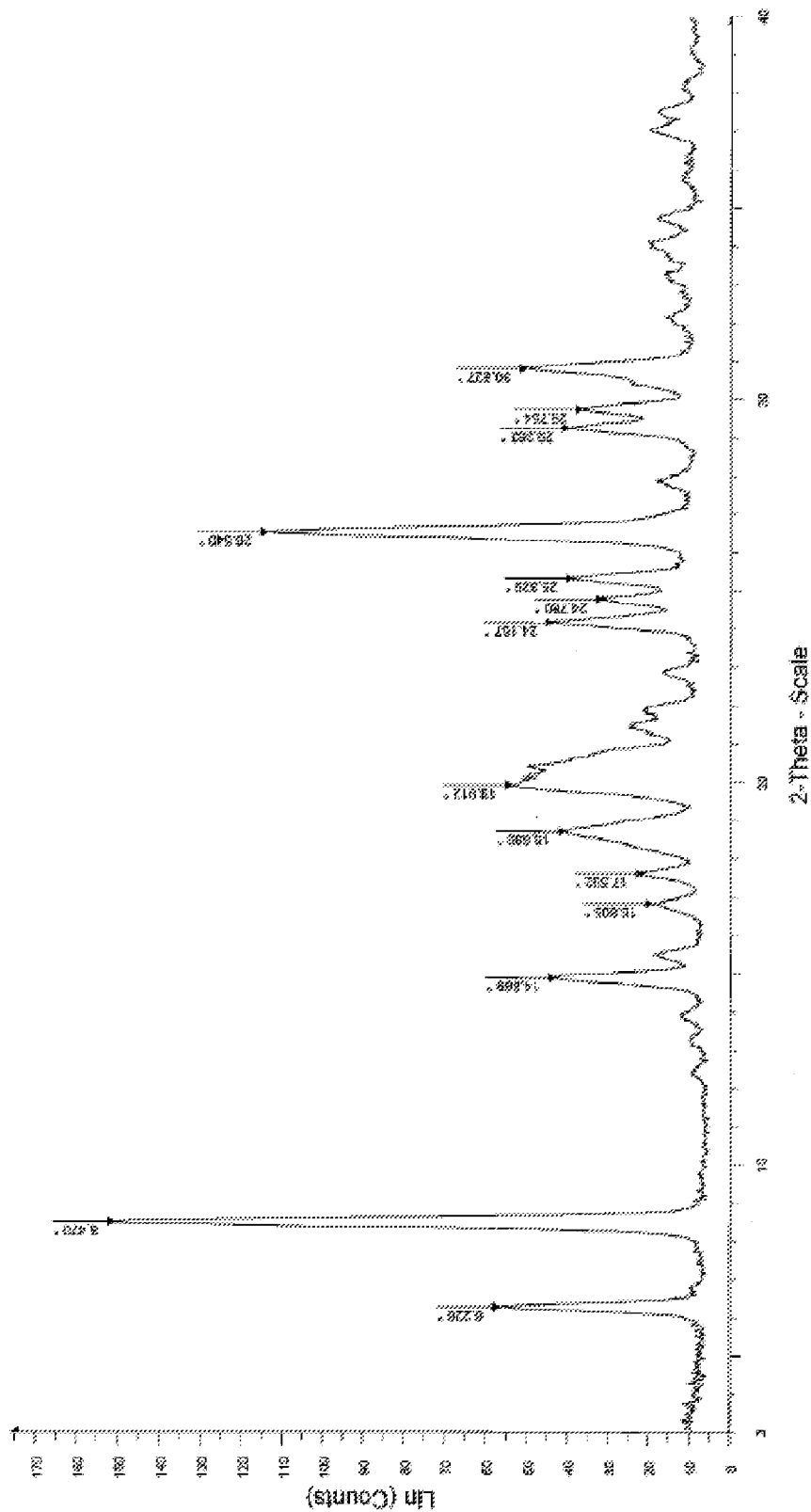
FIG. 3 shows a powder x-ray diffraction diagram of Form 1 monohydrate crystals of a compound represented by formula (1b).
Figure 4:
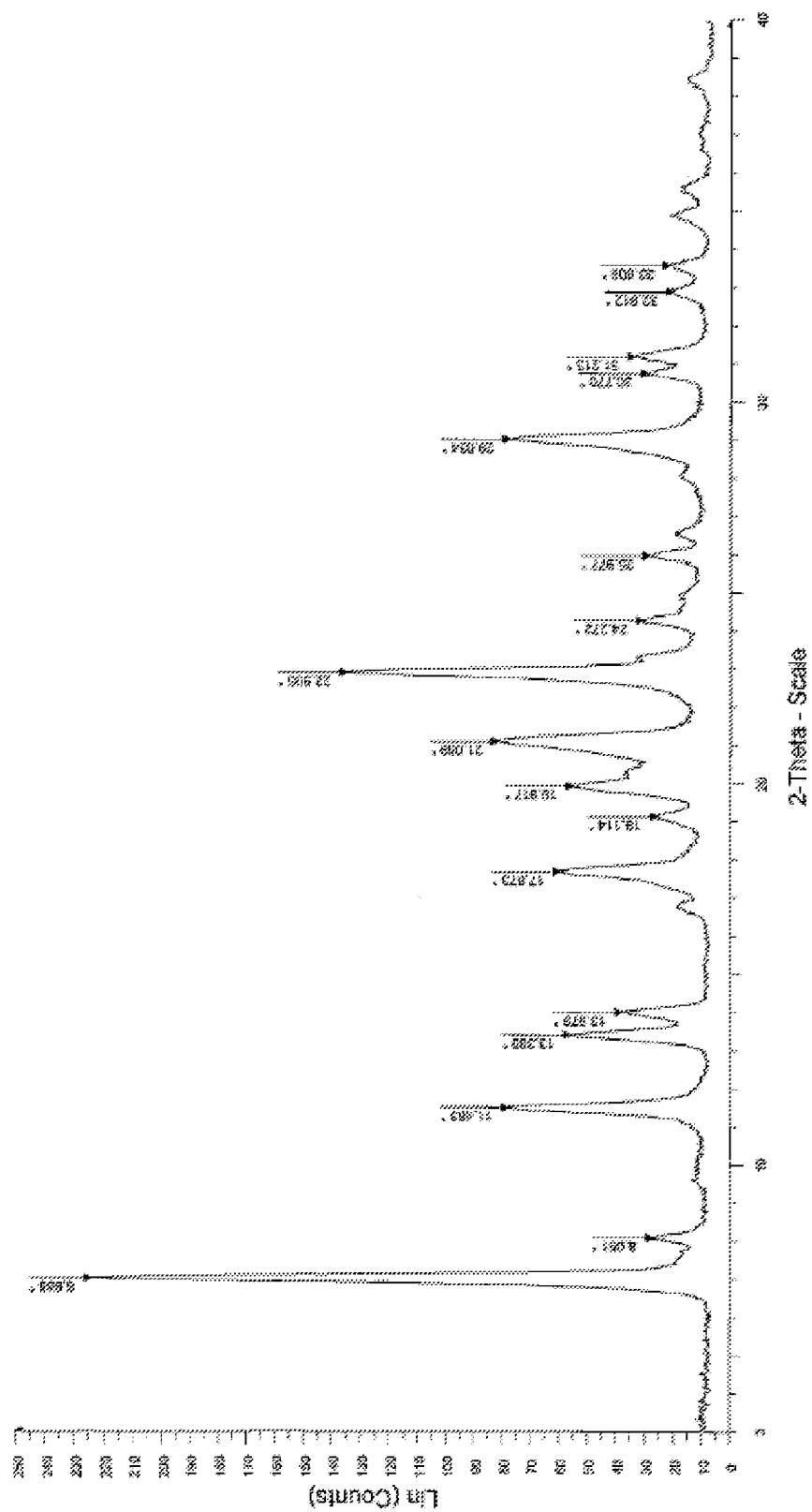
FIG. 4 shows a powder x-ray diffraction diagram of Form 2 monohydrate crystals of the compound represented by formula (1b).
Figure 7:
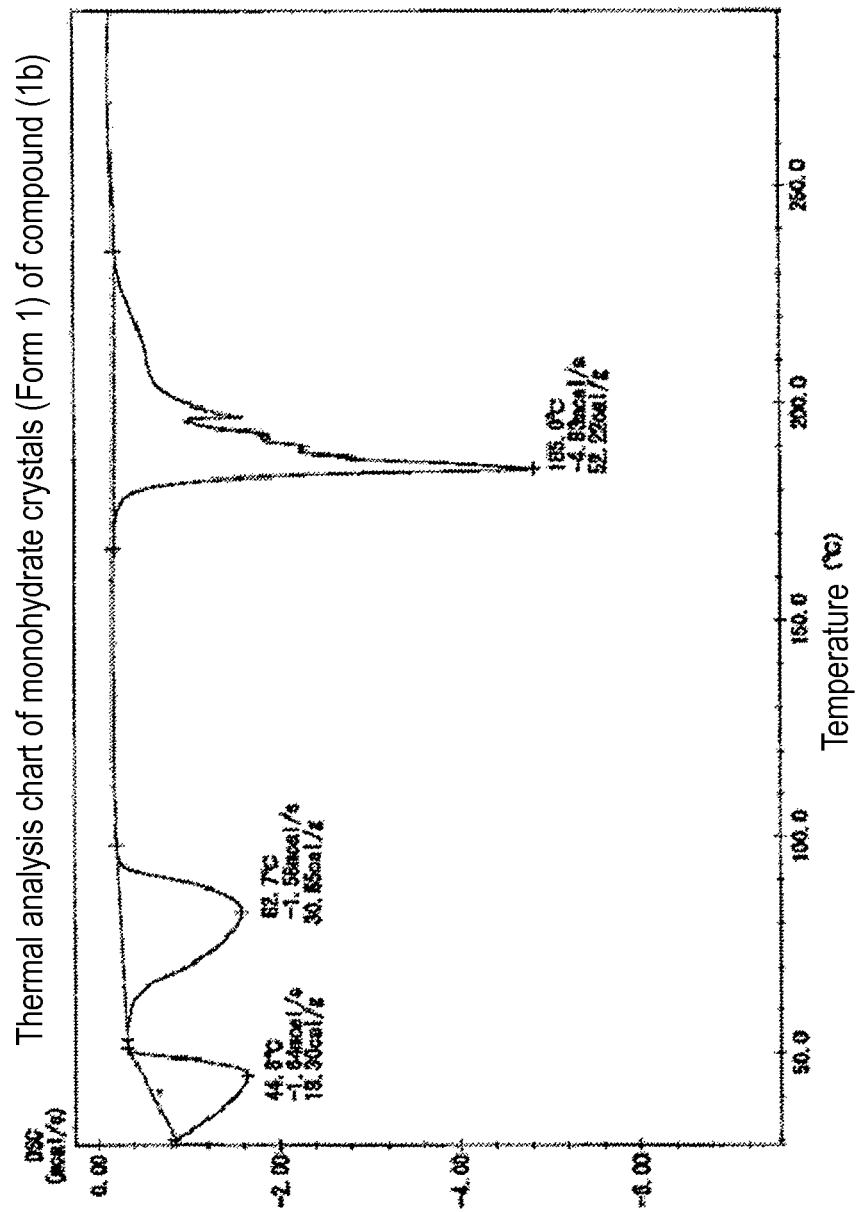
FIG. 7 shows a thermal analysis chart of monohydrate crystals (Form 1) of the compound represented by formula (1b).
Figure 8:
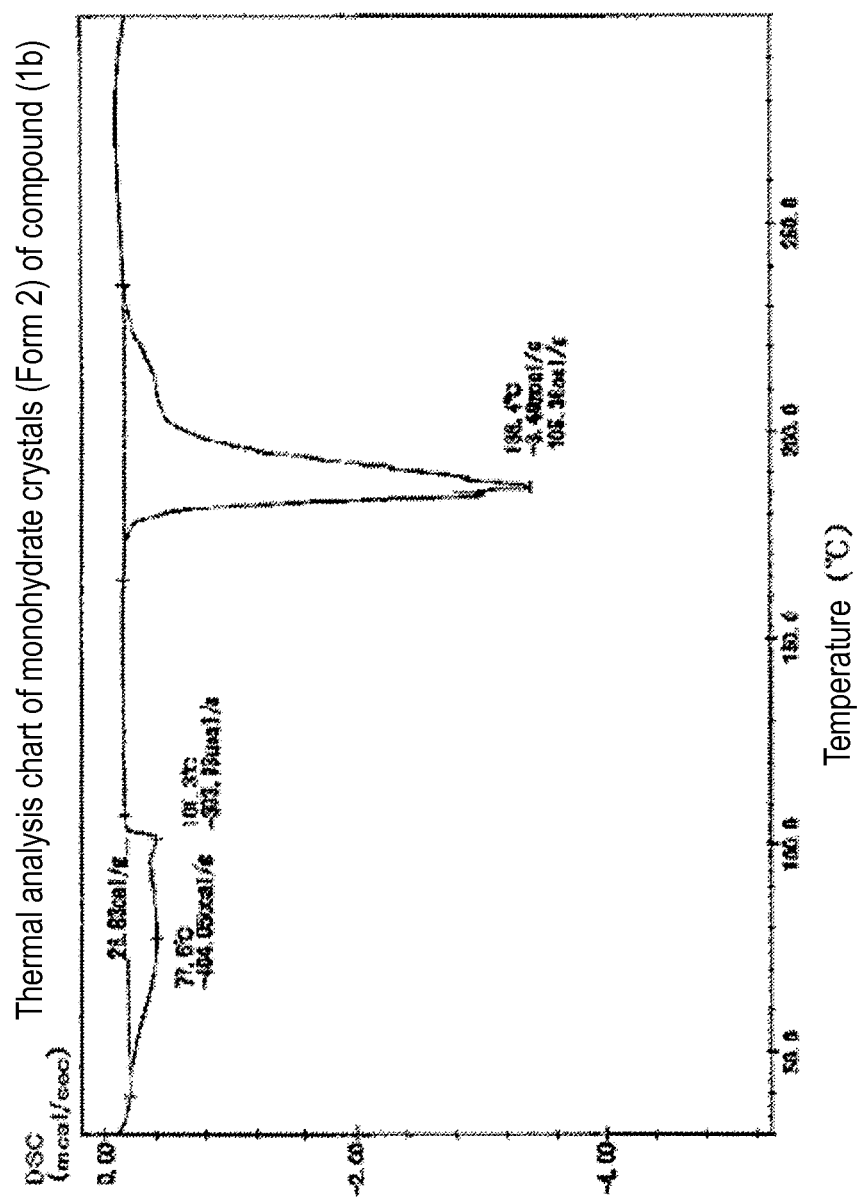
FIG. 8 shows a thermal analysis chart of monohydrate crystals (Form 2) of the compound represented by formula (1b).

Compound (1a) was treated with anhydrous oxalic acid in 6% hydrous acetonitrile to obtain two crystal polymorphs of monohydrate crystals of the title compound represented by formula (1b) (this production method is described in Example 3 below). Powder x-ray diffraction diagrams of the Form 1 and Form 2 monohydrate crystals are shown in FIGS. 3 and 4, respectively, and their diffraction diagrams based on thermal analysis are shown in FIGS. 7 and 8, respectively. The Form 1 monohydrate crystals were found to be transformed to Form 2 monohydrate crystals when left at room temperature for approximately 2 hours, demonstrating that the Form 2 monohydrate crystals are metastable crystals. The Form 1 monohydrate crystals were transformed to the anhydrous crystals of compound (1) by way of crystal transformation to the metastable Form 2 monohydrate crystals, demonstrating that the Form 2 monohydrate crystals are preferable as monohydrate crystals used as a starting material in the production of anhydrous crystals of compound (1).

Example 3

Crystals of tert-butyl {(1R,2S,5S)-2-amino-5-[(dimethylamino)carbonyl]cyclohexyl}carbamate oxalate monohydrate (1b)

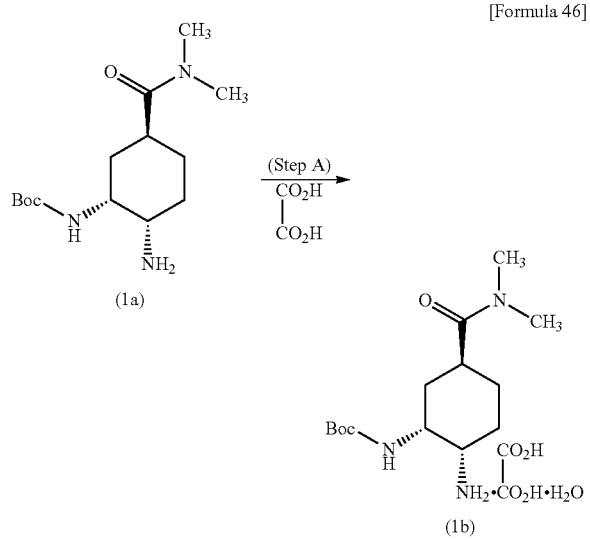

wherein Boc represents a tert-butoxycarbonyl group.

[Step A]

Acetonitrile (595 ml) and water (43 ml) were added to compound (1a) (45.61 g, 0.16 mol), and the mixture was heated to an internal temperature of 50 to 70° C. with stirring. To this solution, a solution prepared in advance from anhydrous oxalic acid (18.87 g, 0.21 mol) and acetonitrile (255 ml) was added dropwise over 1 hour with the internal temperature kept at 50 to 70° C. After completion of the dropwise addition, the reaction mixture was stirred at 50 to 70° C. for 5 hours and then cooled to an internal temperature of 20 to 40° C. The precipitated crystals were collected, washed with acetonitrile, and then dried to obtain monohydrate crystals of the compound represented by formula (1b) (59.14 g, 94.1%). The powder x-ray diffraction diagram of the obtained monohydrate crystals represented by formula (1b) and the results of thermal analysis thereon were the same as those of the Form 2 monohydrate crystals of Example 2 shown in FIGS. 4 and 8.

Example 4

Anhydrous Crystals of tert-butyl {(1R,2S,5S)-2-amino-5-[(dimethylamino)carbonyl]cyclohexyl}carbamate oxalate (1)

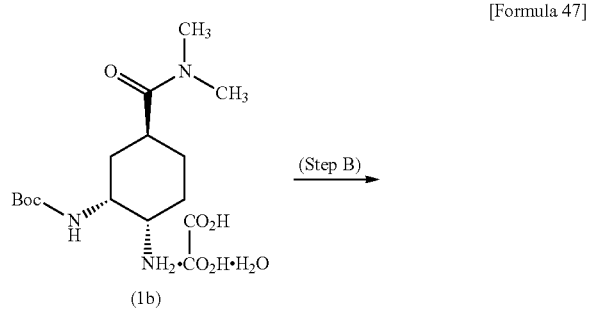

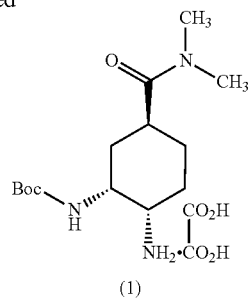

wherein Boc represents a tert-butoxycarbonyl group.

[Step B]

Acetonitrile (126 ml) was added to the monohydrate crystals of the compound represented by formula (1b) (13.25 g, 33.68 mmol). The reaction system was confirmed to have a water content of approximately 0.7%, and then, the mixture was stirred at an internal temperature of 70 to 75° C. for 5 hours. Acetonitrile (66 ml) in the reaction solution was distilled off under reduced pressure with the internal temperature kept at 40 to 70° C. (external temperature: 80° C. or lower). Next, to the reaction mixture, commercially available anhydrous acetonitrile (66 ml) was added in the same amount as the amount distilled off by concentration. Then, the reaction mixture was confirmed to have a water content of approximately 0.15% and then stirred at 50 to 70° C. for 1 hour. The reaction mixture was cooled to an internal temperature of 20 to 40° C. Then, the precipitated crystals were collected by filtration, washed with acetonitrile, and dried to obtain the anhydrous crystals of the title compound represented by formula (1) (12.46 g, 98.6%). The powder x-ray diffraction diagram of the obtained anhydrous crystals of the compound represented by formula (1) and the results of thermal analysis thereon were the same as those of the Form 2 anhydrous crystals of Example 1 shown in FIGS. 2 and 6.

Example 5

Figure 9:
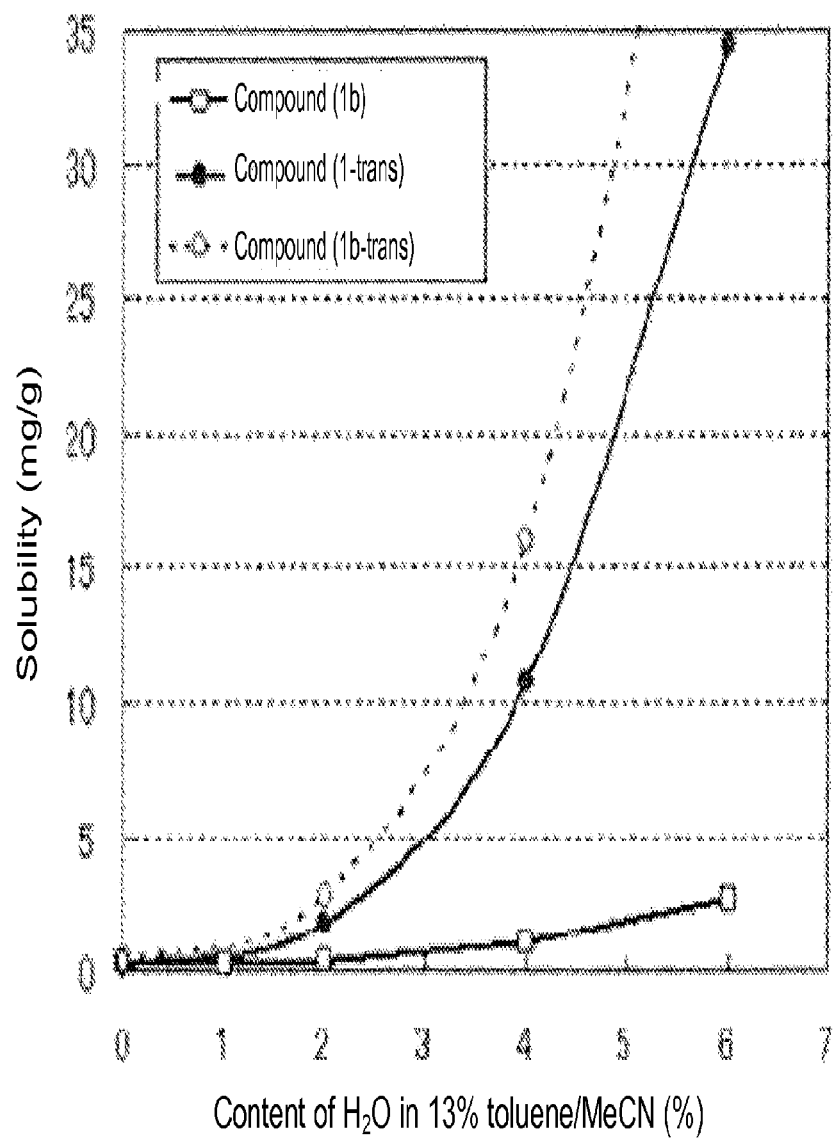
FIG. 9 is a diagram showing a comparison of water solubility among three types of crystals: monohydrate crystals of the compound represented by formula (1b), anhydrous crystals of a trans-isomer represented by formula (1-trans), and monohydrate crystals of a trans-isomer represented by formula (1b-trans).

As shown in FIG. 9, water solubility was compared among crystals of three trans-isomers: the monohydrate crystals of the compound represented by formula (1b), newly prepared monohydrate crystals of a trans-isomer compound represented by formula (1b-trans), and anhydrous crystals of a compound represented by formula (1-trans).

Water was added to a 13% toluene/acetonitrile solution to change the percentage water content to compare water solubility between the monohydrate crystals of the compound represented by formula (1b) and the monohydrate crystals of the trans-isomer compound represented by formula (1b-trans).

<Results>

The monohydrate crystals of the compound represented by formula (1b-trans) were more water-soluble than the monohydrate crystals of the compound represented by formula (1b) in the cis-form. The difference in water solubility between the monohydrate crystals of the compound represented by formula (1b) in the cis-form and the monohydrate crystals of the trans-isomer represented by formula (1b-trans) increased according to the rise in the percentage water content of the solvent. This indicated the possibility of separation between these isomers using a hydrous solvent system by utilizing the difference in water solubility.

Example 6

The percentage of anhydrous crystals of the related trans-isomer compound represented by formula (1-trans) from the first crystallization in the conventional method (the pamphlet of International Publication No. WO 2007/032498) was compared with the percentage content of the trans-isomer (1-trans) in monohydrate crystals of the compound represented by formula (1b) produced by (Method A) of the present invention.

TABLE 3

| Crystallization condition | Conventional method | | Method involving addition of water | |
|---|---|---|---|---|
| | No. 1 | No. 2 | No. 3 | No. 4 |
| Oxalic acid solution dropwise addition condition | 60° C., 2 hr | 60° C., 0.5 hr | 60° C., 1 hr | 60° C., 2 hr |
| Loss into filtrate | | 11% | 9.7% | 10.1% |
| Isomer (1-trans) | 5.11% | 2.01% | 0.25% | 0.97% |

<Results>

(Method A) of the present invention, i.e., the method involving producing monohydrate by the addition of water, significantly reduced the percentage content of the trans-isomer. The operability problems or the like attributed to the time over which the oxalic acid solution was added dropwise did not arise under heating. (Method A) of the present invention lost crystals into the filtrate during their isolation at the same level as in the conventional method. These results demonstrated that (Method A) of the present invention was a process for the preparation of monohydrate crystals of highly pure compound (1).

Example 7

Anhydrous Crystals of tert-butyl {(1R,2S,5S)-2-amino-5-[(dimethylamino)carbonyl]cyclohexyl}carbamate oxalate (1)

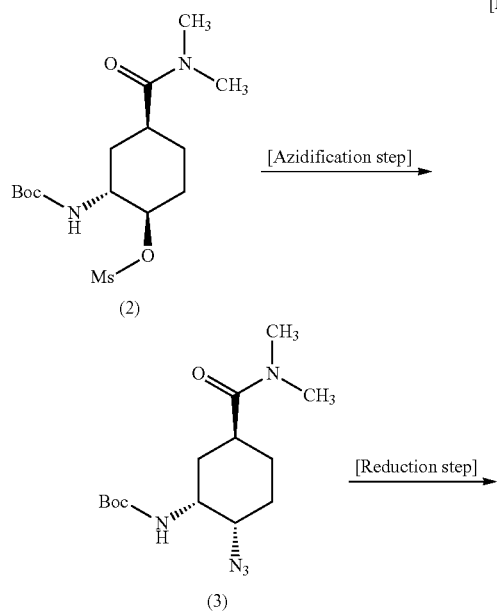

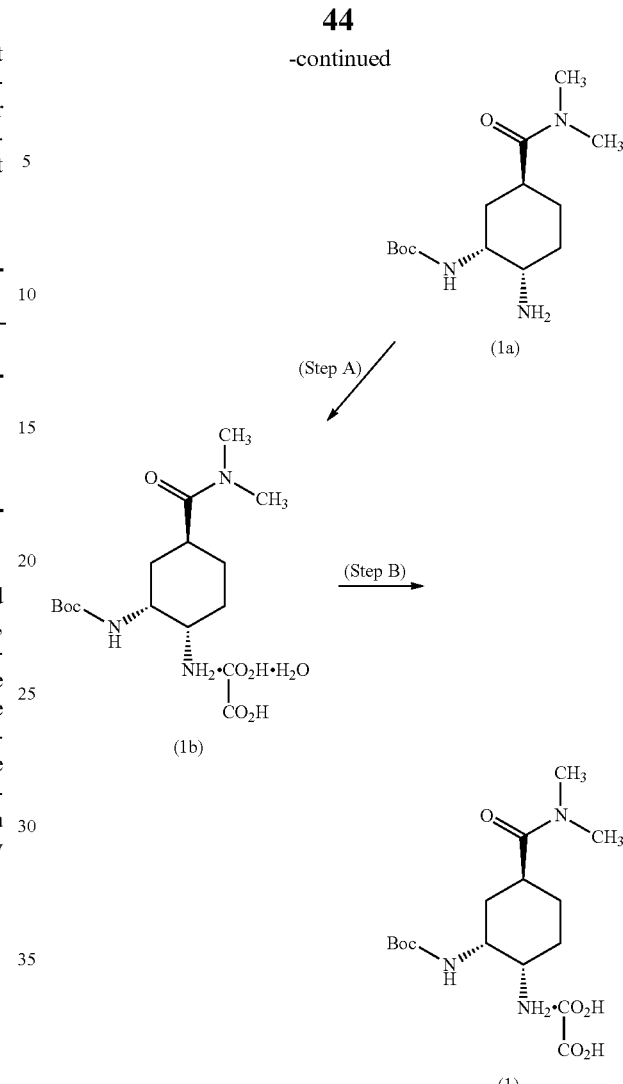

wherein Ms represents a methanesulfonyl group; and Boc represents a tert-butoxycarbonyl group.

[Azidification Step]

Water (184 ml) was added to sodium azide (32.82 g) and dodecylpyridinium chloride (35.83 g), and the mixture was stirred at 60° C. for 1 hour. Toluene (460 ml) was added to the reaction solution, followed by azeotropic dehydration using a Dean-Stark water trap under reduced pressure at this temperature. The toluene suspension was confirmed to have approximately 0.1% water, and then, toluene was added thereto in an amount corresponding to the amount distilled off. (1R,2R,4S)-2-[(tert-butoxycarbonyl)amino]-4-[(dimethylamino)carbonyl]cyclohexylmethanesulfonate (2) was added thereto, and the mixture was stirred at an internal temperature of 60 to 65° C. for 48 hours. The reaction solution was cooled to 40° C., and then, a 5% aqueous sodium bicarbonate solution (460 ml) was added thereto, followed by extraction three times with toluene (184 ml) heated to 40° C. The extracts were combined and washed with twice with water (138 ml) heated to 40° C., and then, the extracts were concentrated into approximately half the volume. The obtained solution of compound (3) in toluene was used in the next step without being further purified.

[Reduction Step]

Methanol (460 ml), commercially available 7.5% palladium-carbon (manufactured by Kawaken Fine Chemicals Co., Ltd.; 12.88 g), and ammonium formate (17.48 g) were added to the solution of compound (3) in toluene obtained in the preceding [Azidification step], and the mixture was stirred in an internal temperature range of 30 to 50° C. for 1 hour. The insoluble metal catalyst was filtered off, and this residue was washed with methanol (184 ml). The filtrate was concentrated under reduced pressure. To the concentrated residue, toluene (230 ml) was added, and the mixture was concentrated under reduced pressure to obtain compound (1a) as a crude product. The obtained compound (1a) as a crude product was used in the next step without being further purified.

[Step A]

Acetonitrile (644 ml) and water (46 ml) were added to compound (1a) obtained in the preceding [Reduction step], and the mixture was heated to an internal temperature of 50 to 70° C. with stirring. To this solution, a solution prepared in advance from anhydrous oxalic acid (18.18 g) and acetonitrile (276 ml) was added dropwise over 1 hour with the internal temperature kept at 50 to 70° C. After completion of the dropwise addition, the reaction mixture was stirred at 50 to 70° C. for 5 hours and then cooled to an internal temperature of 20 to 40° C. The precipitated crystals were collected, washed with acetonitrile (92 ml), and then dried to obtain monohydrate crystals of the compound represented by formula (1b).

[Step B]

Acetonitrile (920 ml) was added to the monohydrate crystals of the compound represented by formula (1b) obtained in the preceding [Step A]. The reaction system was confirmed to have a water content of approximately 0.7%, and then, the mixture was stirred at an internal temperature of 70 to 75° C. for 5 hours. Acetonitrile (526 ml) in the reaction solution was distilled off under reduced pressure with the internal temperature kept at 40 to 70° C. (external temperature: 80° C. or lower). To the reaction mixture, acetonitrile was newly added in the same volume (526 ml) as the amount distilled off. The reaction mixture was confirmed to have a water content of approximately 0.15% and then stirred at 50 to 70° C. for 1 hour. The reaction mixture was cooled to an internal temperature of 20 to 40° C. Then, the precipitated crystals were collected by filtration and dried to obtain the title compound [52.12 g, 55% based on compound (2)].

Example 8

Purity Measurement of $N^1$-(5-chloropyridin-2-yl)-$N^2$-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)ethanediamide mono-p-toluenesulfonate monohydrate (X-a)

The purity of the compound represented by formula (X-a) was measured by HPLC according to the method described in Reference Example 7 using the anhydrous crystals of tert-butyl {(1R,2S,5S)-2-amino-5-[(dimethylamino)carbonyl]cyclohexyl}carbamate oxalate (1) produced in Example 7 of the present invention.

From measurement results of 3 lots in total, the total amount of impurities such as the related compounds was confirmed to be in the range of 0.17 to 0.19% by weight. Thus, the compound represented by formula (X-a) had a purity of 99.81% by weight to 99.83% by weight.

INDUSTRIAL APPLICABILITY

The production method of the present invention can be used as a novel method for industrially producing compound (X) useful as an FXa inhibitor or a pharmacologically acceptable salt thereof, or a hydrate thereof.

The invention claimed is:

1. A process for the preparation of anhydrous crystals of a compound represented by the following formula (1):

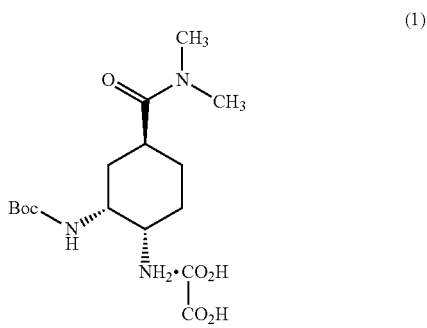

wherein Boc represents a tert-butoxycarbonyl group, the method comprising the steps of:

treating a compound represented by the following formula (1a):

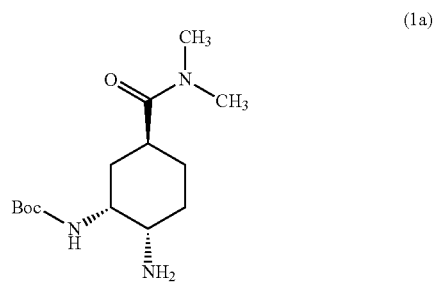 [SMILES: CN(C)C(=O)[C@H]1CC[C@H](N)[C@H](NC(=O)OC(C)(C)C)C1]

wherein Boc is as defined above, with dropwise addition of anhydrous oxalic acid at 50 to 80° C. in a hydrous organic solvent containing 4 to 10% water, and after completion of the dropwise addition, the reaction mixture is further stirred at 50 to 80° C. for 2 to 5 hours to obtain monohydrate crystals of a compound represented by the following formula (1b):

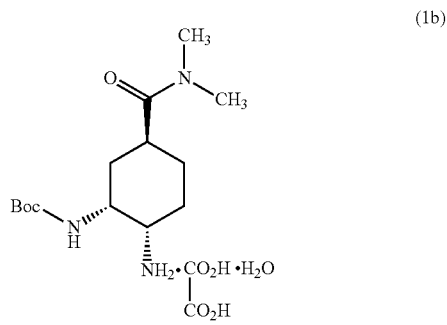

wherein Boc is as defined above; and stirring the monohydrate crystals of the compound represented by formula (1b) in an organic solvent with a water content of less than 1% by weight under heating at 50 to 80° C., wherein the organic solvent is distilled off by ½ to 4/7 of the total volume of the organic solvent under reduced pressure in the range of 40 to 75° C. and then re-adding an organic solvent in an amount corresponding to the amount distilled off.

2. The preparation process according to claim 1, wherein the heating is performed at 70 to 75° C.

3. The preparation process according to claim 1, wherein the water content of the organic solvent is kept at less than 0.2% by weight in the distilling off of the organic solvent under reduced pressure and the re-addition.

4. A process for the preparation of monohydrate crystals of a highly pure compound represented by the following formula (1b):

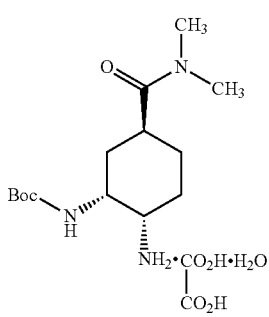

wherein Boc represents a tert-butoxycarbonyl group,
the method comprising treating a compound represented by the following formula (1a):

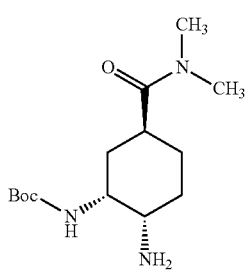

wherein Boc is as defined above,
with dropwise addition of anhydrous oxalic acid at 50 to 80° C. in a hydrous organic solvent containing 4 to 10% water, and after completion of the dropwise addition, the reaction mixture is further stirred at 50 to 80° C. for 2 to 5 hours.

5. The preparation process according to claim 1, wherein the organic solvent is one or two or more solvents selected from the group consisting of C1-C5 alkyl acetate solvents, linear or branched C1-C8 alcohol solvents, C1-C6 ketone solvents, toluene solvents, and C2-C5 nitrile solvents.

6. The preparation process according to claim 1, wherein the organic solvent is acetonitrile, toluene, or a mixed solvent of acetonitrile and toluene.

7. The preparation process according to claim 1, wherein the organic solvent is acetonitrile.

8. The preparation process according to claim 4, wherein the compound represented by formula (1b) has a purity of 97.0% or more.

9. The preparation process according to claim 4, wherein the compound represented by formula (1b) has a purity of 99.0% or more.

10. The preparation process according to claim 1, wherein the compound represented by formula (1) has a purity of 97.0% or more.

11. The preparation process according to claim 1, wherein the compound represented by formula (1) has a purity of 99.0% or more.

12. A process for the preparation of anhydrous crystals of a compound represented by the following formula (1):

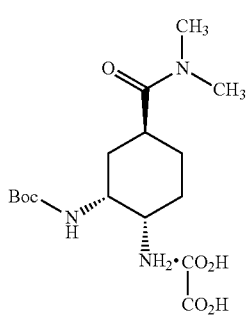

wherein Boc represents a tert-butoxycarbonyl group,
the method comprising the step of stirring monohydrate crystals of a compound represented by the following formula (1b):

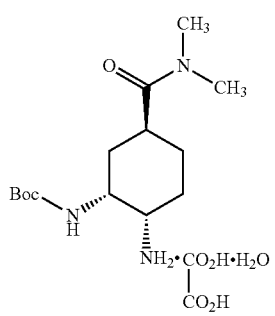

wherein Boc is as defined above,
in an organic solvent with a water content of less than 1% by weight under heating at 50 to 80° C., wherein the organic solvent is distilled off by ½ to 4/7 of the total volume of the organic solvent under reduced pressure in the range of 40 to 75° C. and then re-adding an organic solvent in an amount corresponding to the amount distilled off.

* * * * *